United States Patent
Rosenberger et al.

(10) Patent No.: US 12,233,055 B2
(45) Date of Patent: *Feb. 25, 2025

(54) TOPICAL MONTELUKAST FORMULATIONS

(71) Applicant: TARO PHARMACEUTICAL INDUSTRIES LTD., Haifa Bay (IL)

(72) Inventors: Vered Rosenberger, Givatayim (IL); Helena Shifrin, Rehovot (IL); Irena Oleinik, Karmiel (IL); Tzviel Sheskin, Haifa (IL); Ron Schlinger, Tel Aviv (IL); Avi Avramoff, Haifa (IL)

(73) Assignee: TARO PHARMACEUTICAL INDUSTRIES LTD., Haifa Bay (IL)

(*) Notice: Subject to any disclaimer, the term of this patent is extended or adjusted under 35 U.S.C. 154(b) by 878 days.

This patent is subject to a terminal disclaimer.

(21) Appl. No.: 17/391,813

(22) Filed: Aug. 2, 2021

(65) Prior Publication Data

US 2021/0393613 A1    Dec. 23, 2021

Related U.S. Application Data

(63) Continuation-in-part of application No. 17/165,574, filed on Feb. 2, 2021, now Pat. No. 11,173,117.

(60) Provisional application No. 63/080,744, filed on Sep. 20, 2020, provisional application No. 62/969,333, filed on Feb. 3, 2020.

(51) Int. Cl.
| | |
|---|---|
| A61K 31/47 | (2006.01) |
| A61K 9/00 | (2006.01) |
| A61K 9/107 | (2006.01) |
| A61K 47/10 | (2017.01) |
| A61P 17/04 | (2006.01) |

(52) U.S. Cl.
CPC ............ *A61K 31/47* (2013.01); *A61K 9/0014* (2013.01); *A61K 9/1075* (2013.01); *A61K 47/10* (2013.01); *A61P 17/04* (2018.01)

(58) Field of Classification Search
None
See application file for complete search history.

(56) References Cited

U.S. PATENT DOCUMENTS

| | | |
|---|---|---|
| 10,548,837 B1 | 2/2020 | Avramoff et al. |
| 2001/0025040 A1 | 9/2001 | Poppe et al. |
| 2002/0052388 A1* | 5/2002 | Harris .................. A61P 9/00 514/290 |
| 2005/0187243 A1 | 8/2005 | Niddam-Hildesheim |
| 2011/0124681 A1 | 5/2011 | Schlesinger |
| 2011/0311613 A1 | 12/2011 | Hutchinson |
| 2017/0157108 A1 | 6/2017 | Kwon et al. |
| 2019/0133925 A1 | 5/2019 | Paiement et al. |

FOREIGN PATENT DOCUMENTS

| | | |
|---|---|---|
| CN | 108125908 A | 6/2018 |
| EP | 3178491 A1 | 6/2017 |
| JP | 2016020321 A | 2/2016 |
| WO | 2007/126865 A2 | 11/2007 |
| WO | 2008/105803 A1 | 9/2008 |
| WO | 2008/106081 A1 | 9/2008 |
| WO | 2010/104281 A2 | 9/2010 |
| WO | 2013/058511 A2 | 4/2013 |
| WO | 2015/093847 A1 | 6/2015 |
| WO | 2017/038732 A1 | 3/2017 |
| WO | 2019/007356 A1 | 1/2019 |

OTHER PUBLICATIONS

Hyun Im et al., "Montelukast Nanocrystals for Transdermal Delivery with Improved Chemical Stability," Pharmaceutics 12(1):18 (2019).
Angelova-Fischer et al., "Successful treatment of severe atopic dermatitis with cysteinyl leukotriene receptor antagonist montelukast," Case Report, Acta Dermatoven APA 14(3): 115-119 (2005).
Cheng, et al. "Pharmacokinetics, bioavailability, and safety of montelukast sodium (MK-0476) in healthy males and females," Pharm Res. 13(3):445-448 (1996).
Durgapal et al., "Formulation and Evaluation of in-Situ Nasal Gel of Montelukast Sodium for the Effective Treatment of Asthma," International Journal of Pharmaceutical Sciences and Research 9(7):2792-2799 (2018).
Eichenfield et al., "Safety and efficacy of pimecrolimus (ASM 981) cream 1% in the treatment of mild and moderate atopic dermatitis in children and adolescents," J Am Acad Dermatol. 46(4):495-504 (2002).
Friedmann et al., A double-blind, placebo-controlled trial of montelukast in adult atopic eczema, Clinical and Experimental Allergy 37(10): 1536-1540 (2007).
International Search Report in PCT/US2021/016237, mailed May 10, 2021.
Jullaphant et al., Abstract: "PO-MB08: Colloidal properties of montelukast sodium nasal spray," NanoThailand. A207 (2016).

(Continued)

*Primary Examiner* — Nannette Holloman
(74) *Attorney, Agent, or Firm* — MEDLER FERRO WOODHOUSE & MILLS PLLC

(57) ABSTRACT

The present disclosure provides for topical emulsion comprising about 0.5% to about 10% Montelukast or pharmaceutically acceptable salt thereof; and about 0.4% to about 4% carbomer; wherein particles comprising the Montelukast in the emulsion have D90 of less than about 50 μm, wherein the Montelukast or pharmaceutically acceptable salt thereof is homogeneously dispersed in the emulsion, and wherein the emulsion has a pH of about 3.0 to about 6.5. The present disclosure also provides a topical gel comprising (a) about 0.5% to about 10% Montelukast or pharmaceutically acceptable salt thereof; (b) about 0.2% to about 8% cellulose polymer; and (c) about 80% to about 95% amphiphilic compound; wherein the gel comprises less than 4% water.

11 Claims, No Drawings

(56) References Cited

OTHER PUBLICATIONS

Jullaphant et al., "Montelukast nasal spray: formulation development and in vitro evaluation," Pharm Dev Technol. 24(4):494-503 (2019).
Kim et al., "The Skin Response to Dimethyl Sulfoxide in Normal Persons and Atopy Patients," Korean Journal of Dermatology, 40(1): 8 (2002).
Mohsin, et al. "Formulation and stability of topical water in oil emulsion containing corn silk extract," Tropical Journal of Pharmaceutical Research 15 (6):1115-1121 (2016).
Mougey et al., "Absorption of montelukast is transporter mediated: a common variant of OATP2B1 is associated with reduced plasma concentrations and poor response," Pharmacogenetics and Genomics, 19(2): 129-138 (2009).
Nerella et al., "Formulation and evaluation of in-situ mucoadhesive nasal gel of montelukast sodium," Der Pharmacia Sinica 5(2):1-8 (2014).
Non-Final Office Action issued in U.S. Appl. No. 16/738,482, dated Mar. 19, 2021.
Rackal (III) et al., "The Treatment of Atopic Dermatitis and Other Dermatoses with Leukotriene Antagonists," Skin Therapy, (9)2: 1-12 (2004).
Riccioni et al., "Brief Review: Advances in Therapy with Antileukotriene Drugs," Annals of Clinical & Laboratory Science, 34(4): 379-387 (2004).
Steinke et al., "Leukotriene Synthesis Inhibitors Versus Antagonists: The Pros and Cons," Current Allergy and Asthma Reports, 7: 126-133 (2007).
Final Office Action issued in U.S. Appl. No. 16/738,482, mailed Nov. 23, 2021.
Djupesland, "Nasal drug delivery devices: characteristics and performance in a clinical perspective—a review," Drug Deliv Transl Res. 3(1):42-62 (2013).
Non-final Office Action issued in U.S. Appl. No. 16/738,482, mailed Oct. 5, 2022.

\* cited by examiner

TOPICAL MONTELUKAST FORMULATIONS

FIELD OF THE INVENTION

The present disclosure provides for topical emulsion comprising about 0.5% to about 10% Montelukast or pharmaceutically acceptable salt thereof; and about 0.4% to about 4% carbomer; wherein particles comprising the Montelukast in the emulsion have D90 of less than about 50 µm, wherein the Montelukast or pharmaceutically acceptable salt thereof is homogeneously dispersed in the emulsion, and wherein the emulsion has a pH of about 3.0 to about 6.5. The present disclosure also provides a topical gel comprising (a) about 0.5% to about 10% Montelukast or pharmaceutically acceptable salt thereof; (b) about 0.2% to about 8% cellulose polymer; and (c) about 80% to about 95% amphiphilic compound; wherein the gel comprises less than 4% water.

BACKGROUND

Atopic dermatitis is an increasingly common pruritic, chronic, inflammatory skin disorder. There has been a striking rise in the incidence of Atopic dermatitis (AD) during the past two decades, which is not simply due to an increased recognition of the disease. Population studies suggest that in most countries, AD now affects at least 10-20% of children at some point during childhood. In particular, higher prevalence has been recorded in urban regions than in rural regions of development countries, and the disease is more common in higher social class groups, suggesting that environmental factors associated with more industrialized and urban living determine expression of AD.

The major function of the skin is to protect the body against physical and chemical injury and to prevent loss of body water and other substances. The stratum corneum (SC) is the outmost layer of the skin which is being continually replaced. By so doing the skin is well adapted to its requirements for repairing damage from wear and tear. However, in Atopic Dermatitis environmental and individual factors interact in a complex manner to induce skin abnormalities and dryness. Application of moisturizers to the skin induces changes in its superficial as well as deep layers. The chemical and physical characteristics of the individual ingredients of the formulation determine the performance of the drug product. Moreover, in topical treatments of dermatological conditions the efficacy is likely to depend on the dosage, where compliance is a great challenge faced in the management of the diseases.

Montelukast sodium exerts challenges when being formulated, including stability challenges and permeation challenges.

SUMMARY OF THE INVENTION

The present disclosure is directed to a topical emulsion and a topical gel that are stable for an extended period of time. In some embodiments, the disclosure is directed to a topical emulsion comprising (a) about 0.5% to about 10% Montelukast or pharmaceutically acceptable salt thereof; and (b) about 0.4% to about 4% carbomer; wherein particles comprising the Montelukast in the emulsion have a D90 of less than about 50 µm, wherein the Montelukast or pharmaceutically acceptable salt thereof is homogeneously dispersed in the emulsion, and wherein the emulsion has a pH of about 3.0 to about 6.5.

In some embodiments, the particles comprising the Montelukast in the emulsion have D90 of less than about 40 µm. In some embodiments, the particles comprising the Montelukast in the emulsion have D90 of less than about 20 µm. In some embodiments, the particles comprising the Montelukast in the emulsion have D90 of greater than about 8 µm. In some embodiments, the particles comprising the Montelukast in the emulsion have D90 of about 10 µm to about 14 µm.

In some embodiments, the particles comprising the Montelukast in the emulsion have D50 of less than about 30 µm. In some embodiments, the particles comprising the Montelukast in the emulsion have D50 of less than about 25 µm. In some embodiments, the particles comprising the Montelukast in the emulsion have D50 of less than about 15 µm. In some embodiments, the particles comprising the Montelukast in the emulsion have D50 of less than about 5 µm.

In some embodiments, the particles comprising the Montelukast in the emulsion have D10 of less than about 7 µm. In some embodiments, the particles comprising the Montelukast in the emulsion have D10 of greater than about 3 µm. In some embodiments, the particles comprising the Montelukast in the emulsion have D10 of about 4 µm to about 6 µm. In some embodiments, the average particle size of the particles does not change greater than 10% over a period of 3 months at 25° C. In some embodiments, the Montelukast in the particles is Montelukast acid Form I. In some embodiments, the emulsion comprises about 4% to about 8% Montelukast.

In some embodiments, the emulsion comprises about 40% to about 70% water. In some embodiments, the emulsion further comprises a penetration enhancer. In some embodiments, the penetration enhancer is DMSO. In some embodiments, the emulsion comprises less than 5% DMSO. In some embodiments, the emulsion comprises less than 3% DMSO.

In some embodiments, the emulsion comprises less than 10% alcohol. In some embodiments, the emulsion comprises less than 5% alcohol. In some embodiments, the emulsion comprises less than 2% $C_1$-$C_5$ alcohol.

In some embodiments, the topical emulsion further comprises a preservative, an amphiphilic compound, an emulsifier, a lubricant, or combinations thereof. In some embodiments, the preservative is an antioxidant. In some embodiments, the antioxidant comprises BHT, BHA or combinations thereof.

In some embodiments, the amphiphilic compound comprises oleyl alcohol, polyoxyglycerides, propylene carbonate, propylene glycol, or combinations thereof. In some embodiments, the amphiphilic compound is propylene glycol. In some embodiments, the emulsifier is a polysorbate. In some embodiments, the lubricant is polypropylene glycol stearyl ether.

In some embodiments, the total impurities in the emulsion are less than 2% after 12 months at 25° C. In some embodiments, the total impurities in the emulsion are less than 1% after 12 months at 25° C. In some embodiments, the total impurities in the emulsion are less than 0.5% after 12 months at 25° C. In some embodiments, the sulfoxide impurity in the emulsion is less than 2% after 12 months at 25° C. In some embodiments, the sulfoxide impurity in the emulsion is less than 1% after 12 months at 25° C. In some embodiments, the sulfoxide impurity in the emulsion is less than 0.5% after 12 months at 25° C. In some embodiments, the cis-isomer impurity in the emulsion is less than 1% after 12 months at 25° C. In some embodiments, the cis-isomer impurity in the emulsion is less than 0.1% after 12 months at 25° C. In some embodiments, the methylstyrene impurity in the emulsion is less than 0.2% after 12 months at 25° C.

In some embodiments, the emulsion has a maximum globule size of less than about 100 μm. In some embodiments, the emulsion has a maximum globule size of less than about 20 μm.

In some embodiments, the disclosure provides a method of treating atopic dermatitis comprising administering the topical emulsion of the present disclosure.

In some embodiments, the disclosure is directed to a topical gel. In some embodiments, the disclosure provides a topical gel comprising (a) about 0.5% to about 10% Montelukast or pharmaceutically acceptable salt thereof; (b) about 0.2% to about 8% cellulose polymer; and (c) about 80% to about 95% amphiphilic compound; wherein the gel comprises less than 4% water.

In some embodiments, the gel comprises about 4% to about 8% Montelukast.

In some embodiments, the gel comprises less than 1% $C_1$-$C_5$ alcohol. In some embodiments, the gel does not contain $C_1$-$C_5$ alcohol. In some embodiments, the gel comprises less than 2% water. In some embodiments, the gel comprises less than 1% water. In some embodiments, the gel is anhydrous.

In some embodiments, the gel does not comprise a preservative.

In some embodiments, the cellulose polymer comprises hydroxyethylcellulose and hydroxypropyl methylcellulose. In some embodiments, the cellulose polymer comprises hydroxypropyl methylcellulose. In some embodiments, the cellulose polymer comprises hydroxypropyl cellulose. In some embodiments, the gel comprises about 2% to about 6% cellulose polymer. In some embodiments, the gel comprises about 3% to about 4% cellulose polymer.

In some embodiments, the amphiphilic compound comprises oleyl alcohol, polyoxyglycerides, propylene carbonate, propylene glycol, or combinations thereof. In some embodiments, the amphiphilic compound comprises propylene glycol. In some embodiments, the gel comprises about 85% to about 95% amphiphilic compound.

In some embodiments, total impurities in the gel are less than 0.5% after 3 months at 25° C. In some embodiments, the sulfoxide impurity in the gel is less than 0.5% after 3 months at 25° C. In some embodiments, the cis-isomer impurity in the gel is less than 0.1% after 3 months at 25° C. In some embodiments, the methylstyrene impurity in the gel is less than 0.2% after 3 months at 25° C.

In some embodiments, the disclosure provides a method of treating atopic dermatitis comprising administering the topical gel of the present disclosure.

In some embodiments, the disclosure provides a method of reducing the IGA score in a subject suffering from atopic dermatitis, the method comprising topically administering to the subject a Montelukast formulation comprising at least 1% (wt/wt) Montelukast or pharmaceutically acceptable salt thereof for at least 10 days, e.g., at least 14 days, wherein the IGA score is reduced by at least 5% from placebo.

In some embodiments, the disclosure provides a method of reducing the BSA score in a subject suffering from atopic dermatitis, the method comprising topically administering to the subject a Montelukast formulation comprising at least 1% (wt/wt) Montelukast or pharmaceutically acceptable salt thereof for at least 10 days, e.g., at least 14 days, wherein the BSA score is reduced by at least 5% from placebo.

In some embodiments, the disclosure provides a method of reducing erythema in a subject suffering from atopic dermatitis, the method comprising topically administering to the subject a Montelukast formulation comprising at least 1% (wt/wt) Montelukast or pharmaceutically acceptable salt thereof for at least 10 days, e.g., at least 14 days, wherein the erythema is reduced by at least 5% from placebo.

In some embodiments, the disclosure provides a method of reducing induration in a subject suffering from atopic dermatitis, the method comprising topically administering to the subject a Montelukast formulation comprising at least 1% (wt/wt) Montelukast or pharmaceutically acceptable salt thereof for at least 10 days, e.g., at least 14 days, wherein the induration is reduced by at least 5% from placebo.

In some embodiments, the disclosure provides a method of reducing lichenification in a subject suffering from atopic dermatitis, the method comprising topically administering to the subject a Montelukast formulation comprising at least 1% (wt/wt) Montelukast or pharmaceutically acceptable salt thereof for at least 10 days, e.g., at least 14 days, wherein the lichenification is reduced by at least 5% from placebo.

In some embodiments, the disclosure provides a method of reducing pruritus in a subject suffering from atopic dermatitis, the method comprising topically administering to the subject a Montelukast formulation comprising at least 1% (wt/wt) Montelukast or pharmaceutically acceptable salt thereof for at least 10 days, e.g., at least 14 days, wherein the pruritus is reduced by at least 5% from placebo.

In some embodiments, the disclosure provides methods as described herein, wherein the Montelukast formulation is the topical emulsion or the topical gel as described herein.

In some embodiments, the disclosure provides a stable topical formulation comprising about 0.5% to about 10% Montelukast or pharmaceutically acceptable salt thereof; wherein the total impurities resulting from the degradation of Montelukast in the composition are less than 2% after 6, 12, 24 or 36 months. In some embodiments, a sulfoxide impurity in the stable topical formulation is less than 2% after 12, 24 or 36 months at 25° C. and 60% humidity. In some embodiments, a cis-isomer impurity in the stable topical formulation is less than 1% after 12, 24 or 36 months at 25° C. and 60% humidity. In some embodiments, a methylstyrene impurity in the stable topical formulation is less than 0.2% after 12, 24 or 36 months at 25° C. and 60% humidity. In some embodiments, the total impurities resulting from the degradation of Montelukast in the composition are less than 2% after 6 months at 40° C. and 75% humidity. In some embodiments, sulfoxide impurity in the formulation is less than 2% after 6 months at 40° C. and 75% humidity. In some embodiments, the cis-isomer impurity in the formulation is less than 1% after 6 months at 40° C. and 75% humidity. In some embodiments, the methylstyrene impurity in the formulation is less than 0.2% after 6 months at 40° C. and 75% humidity.

In some embodiments, the Montelukast is homogenously dispersed in the stable topical formulation for at least about 1 month. In some embodiments, the stable topical formulation is a gel. In some embodiments, the stable topical formulation is an emulsion. In some embodiments, the particle size of particles comprising Montelukast in the emulsion have a D90 of less than about 50 μm and greater than 5 μm, In some embodiments, the particle size of particles comprising Montelukast in the emulsion does not change greater than 20% over a period of three months at 25° C.

In some embodiments, the disclosure provides a method of treating atopic dermatitis (AD) in a population of subjects, the method comprising administering a topical pharmaceutical composition comprising 6.5% of Montelukast to a subject in the population of subjects, wherein the administration of the composition results in an improvement in one or more of the following parameters (a) a decrease from baseline in mean Investigator's Global Assessment (IGA) score of at least 20%, (b) a decrease from baseline in mean % Body Surface Area (BSA) affected score of at least 20%, (c) a decrease from baseline in mean Erythema score of at least 20%, (d) a decrease from baseline in mean Induration score of at least 15%, (e) a decrease from baseline in mean Lichenification score of at least 25%, and (f) a decrease from baseline in mean Pruritus score of at least 20%.

In some embodiments, the disclosure provides a method of treating atopic dermatitis (AD) in a population of subjects, the method comprising administering a topical pharmaceutical composition comprising 6.5% of Montelukast to a subject in the population of subjects, wherein the administration of the composition results in an improvement in one or more of the following parameters (a) ≥10% difference between active and placebo in % reduction from baseline for mean Investigator's Global Assessment score, (b) ≥10% difference between active and placebo in % reduction from baseline for mean % Body Surface Area affected score, (c) ≥10% difference between active and placebo in % reduction from baseline for mean Erythema score, (d) ≥10% difference between active and placebo in % reduction from baseline for mean Induration score, (e) ≥10% difference between active and placebo in % reduction from baseline for mean Lichenification score, and (f) ≥10% difference between active and placebo in % reduction from baseline for mean Pruritus score.

In some embodiments, the disclosure provides method of treating atopic dermatitis (AD) in a population of subjects, the method comprising administering a topical pharmaceutical composition comprising 6.5% of Montelukast to a subject in the population of subjects, wherein the administration of the composition to the subject results in an improvement in one or more of the following parameters (a) the percentage reduction from baseline in mean IGA score in the population of subjects is at least 5% higher than the percentage reduction in mean IGA score in a separate population of subjects treated with placebo, (b) the percentage reduction from baseline in mean % BSA affected score in the population of subjects is at least 5% higher than the percentage reduction in mean % BSA affected score in a separate population of subjects treated with placebo, (c) the percentage reduction from baseline in mean Erythema score in the population of subjects is at least 5% higher than the percentage reduction in mean Erythema score in a separate population of subjects treated with placebo, (d) the percentage reduction from baseline in mean Induration score in the population of subjects is at least 5% higher than the percentage reduction in mean Induration score in a separate population of subjects treated with placebo, (e) the percentage reduction from baseline in mean Lichenification score in the population of subjects is at least 5% higher than the percentage reduction in mean Lichenification score in a separate population of subjects treated with placebo, and (f) the percentage reduction from baseline in mean Pruritus score in the population of subjects is at least 5% higher than the percentage reduction in mean Pruritus score in a separate population of subjects treated with placebo.

In some embodiments, the disclosure provides a method of treating atopic dermatitis (AD) in a population of subjects, the method comprising administering a topical pharmaceutical composition comprising 6.5% of Montelukast to a subject in the population of subjects, wherein the administration of the composition results in an improvement in one or more of the following parameters (a) at least a 75% reduction from baseline mean IGA score, (b) at least an 85% reduction from baseline mean % BSA Affected score, (c) at least a 90% reduction from baseline mean Erythema score, (d) at least a 90% reduction from baseline mean Induration score, (e) at least a 90% reduction from baseline mean Lichenification score, and (f) at least an 85% reduction from baseline mean Pruritus score.

In some embodiments, the disclosure provides a method of treating atopic dermatitis (AD) in a population of subjects, the method comprising administering to the population of subjects twice daily a topical pharmaceutical composition comprising 6.5% of Montelukast, wherein the administration of the composition to the population of subjects results in an improvement in one or more of the following parameters (a) the percentage of subjects with a 2- or more grade improvement from baseline is at least 5% higher than placebo in Investigator's Global Assessment (IGA) score, (b) the percentage of subjects with a 2- or more grade improvement from baseline is at least 5% higher than placebo in Erythema score, (c) the percentage of subjects with a 1- or more grade improvement from baseline is at least 5% higher than placebo in Induration score, (d) the percentage of subjects with a 2- or more grade improvement from baseline is at least 5% higher than placebo in Lichenification score, and (e) the percentage of subjects with a 3- or more grade improvement from baseline is at least 5% higher than placebo in Pruritus score.

In some embodiments, the disclosure provides a method of treating atopic dermatitis (AD) in a subject, the method comprising administering a topical pharmaceutical composition comprising 6.5% of Montelukast to the subject, wherein the administration results in a reduction of at least one symptom selected from erythema, pruritus, induration and lichenification compared to a placebo as measured by a success profile comprising at least a 2-grade improvement from baseline of the symptoms.

In some embodiments, the disclosure provides a method of treating mild-to-moderate atopic dermatitis (AD) in a patient, the method comprising administering a topical pharmaceutical composition comprising 6.5% of montelukast or its pharmaceutically acceptable salt, twice daily to the patient, wherein the administration of the composition to the patient achieves an Investigator's Global Assessment (IGA) or Investigator's static Global Assessment (ISGA) of "clear" (score=0) or "almost clear" (score=1) with at least two-grade reduction from baseline within week 4 of treatment.

In some embodiments, the subject is ≥6 months of age. In some embodiments, the subject is ≥12 years of age. In some embodiments, the subject is ≥18 years of age. In some embodiments, the subject is ≥3 months of age.

DETAILED DESCRIPTION

The present disclosure provides for topical formulations of Montelukast or pharmaceutically acceptable salt thereof. In some embodiments, the disclosure provides for a topical emulsion that comprising (a) about 0.5% to about 10% Montelukast or pharmaceutically acceptable salt thereof; and (b) about 0.4% to about 4% carbomer; wherein particles comprising the Montelukast in the emulsion have D90 of less than about 50 μm, wherein the Montelukast or pharmaceutically acceptable salt thereof is homogeneously dispersed in the emulsion, and wherein the emulsion has a pH of about 3.0 to about 6.5. Applicant has found that the topical emulsions provided herein are both physically and chemically stable over extended periods of time at room temperature, or at accelerated conditions.

In some embodiments, the disclosure provides for a topical gel comprising (a) about 0.5% to about 10% Montelukast or pharmaceutically acceptable salt thereof; (b) about 0.2% to about 8% cellulose polymer; and (c) about 80% to about 95% amphiphilic compound; wherein the gel comprises less than 4% water. Applicant has found that the topical gels provided herein are both physically and chemically stable over extended periods of time at room temperature, or at accelerated conditions.

As used herein, "a" or "an" may mean one or more. As used herein, when used in conjunction with the word "comprising," the words "a" or "an" may mean one or more than one. As used herein, "another" or "a further" may mean at least a second or more.

Throughout this application, the term "about" is used to indicate that a value includes the inherent variation of error for the method/device being employed to determine the value, or the variation that exists among the study subjects. Typically, the term "about" is meant to encompass approximately or less than 1%, 2%, 3%, 4%, 5%, 6%, 7%, 8%, 9%, 10%, 11%, 12%, 13%, 14%, 15%, 16%, 17%, 18%, 19% or 20% or higher variability, depending on the situation. In some embodiments, one of skill in the art will understand the level of variability indicated by the term "about," due to the context in which it is used herein. It should also be understood that use of the term "about" also includes the specifically recited value.

The use of the term "or" in the claims is used to mean "and/or," unless explicitly indicated to refer only to alternatives or the alternatives are mutually exclusive, although the disclosure supports a definition that refers to only alternatives and "and/or."

As used herein, the terms "comprising" (and any variant or form of comprising, such as "comprise" and "comprises"), "having" (and any variant or form of having, such as "have" and "has"), "including" (and any variant or form of including, such as "includes" and "include") or "containing" (and any variant or form of containing, such as "contains" and "contain") are inclusive or open-ended and do not exclude additional, unrecited elements or method steps. It is contemplated that any embodiment discussed in this specification can be implemented with respect to any composition (e.g., formulation, emulsion or gel) or method of the present disclosure. Furthermore, compositions (e.g., formulations, emulsion or gel) of the present disclosure can be used to achieve methods of the present disclosure.

The use of the term "for example" and its corresponding abbreviation "e.g." (whether italicized or not) means that the specific terms recited are representative examples and embodiments of the disclosure that are not intended to be limited to the specific examples referenced or cited unless explicitly stated otherwise.

As used herein, "between" is a range inclusive of the ends of the range. For example, a number between x and y explicitly includes the numbers x and y, and any numbers that fall within x and y.

As used herein, "D10" is defined as the size value corresponding to cumulative size distribution at 10%, which represents the size of particles below which 10% of the sample lies.

As used herein, "D50" is defined as the size value corresponding to cumulative size distribution at 50%, which represents the size of particles below which 50% of the sample lies.

As used herein, "D90" is defined as the size value corresponding to cumulative size distribution at 90%, which represents the size of particles below which 90% of the sample lies.

As used herein, "formulation stability" refers to chemical stability, physical stability or both chemical and physical stability.

The term Montelukast refers to [R-(E)]-1-[[[1-[2-(7-chloro-2-quinolinyl)-ethenyl]-phenyl]-3-[2-(1-hydroxy-1-methylethyl)phenyl]propyl]thio]methyl]cyclopropane acetic acid (Montelukast) or a pharmaceutically acceptable salt thereof. For simplicity, as used herein, the term Montelukast includes the designated chemical entity as well as, at times, its pharmaceutically acceptable salt.

In some embodiments, the Montelukast is in the form of a salt. Suitable Montelukast salts can include an alkali metal salt such as sodium or potassium, an alkaline earth salt, or an ammonium salt. In some embodiments, the Montelukast can be a free acid. In some embodiments, the Montelukast can be a monosodium salt, as represented as

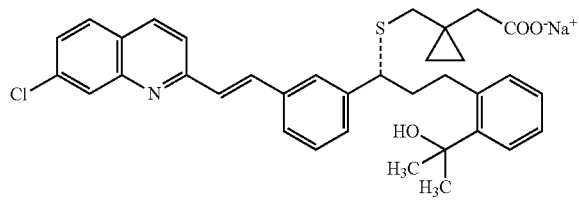

In some embodiments, the Montelukast is added as a salt or free acid when preparing emulsion or gel formulations, and then become a free acid once in its final dosage form. In some embodiments, the Montelukast crystal particles comprise the free acid form, e.g., Form I.

Topical Emulsion

The present disclosure provides for a topical emulsion comprising Montelukast or pharmaceutically acceptable salt thereof. Montelukast is known to be stable at high pH solutions, e.g., in pH above 7. The present disclosure provides for an emulsion which is compatible with the pH of the skin, i.e., pH of around 3 to 6.5, while keeping Montelukast physically and chemically stable in the emulsion. Additionally, the present disclosure provides an emulsion in which the Montelukast, with a molecular weight of greater 600, is able to achieve skin penetration in an amount to be therapeutically effective. The present disclosure provides a topical emulsion suitable for application to the skin without undue irritation, while maintain the physical stability, chemical stability and efficacy of the Montelukast.

In some embodiments, the disclosure provides a topical emulsion having Montelukast or pharmaceutically acceptable salt thereof of a defined particle size. Applicant has found that, in some embodiments, emulsions comprising the Montelukast particles are physically stable, wherein the particles remain homogeneously dispersed in the topical emulsion, and wherein the average size of Montelukast particles does not change over an extended period of time.

In some embodiments, particles comprising the Montelukast in the emulsion have D90 of less than about 50 µm, less than about 40 µm, less than about 35 µm, less than about 30 µm, less than about 25 µm, less than about 20 µm, or less than about 15 µm. In some embodiments, particles comprising the Montelukast in the emulsion have D50 of less than about 30 µm, less than about 25 µm, less than about 20 µm, less than about 15 µm, or less than about 10 µm. In some embodiments, particles comprising the Montelukast in the emulsion have a D90 of less than about 40 µm and a D50 of less than about 25 µm, D90 less than about 35 µm and a D50 of less than about 25 µm, D90 less than about 30 µm and a D50 of less than about 20 µm, D90 less than about 25 µm and a D50 of less than about 15 µm, or D90 of less than about 20 µm and a D50 of less than about 15 µm.

In some embodiments, particles comprising the Montelukast in the emulsion have D90 of less than about 50 µm and greater than 5 µm, less than about 40 µm and greater than 10 µm, less than about 30 µm and greater than 10 µm, less than about 20 µm and greater than 10 µm. In some embodiments, particles comprising the Montelukast in the emulsion have D50 of less than about 30 µm and greater than 2 µm, less than about 25 µm and greater than 3 µm, less than about 20 µm and greater than 4 µm, less than about 15 µm and greater than 5 µm. In some embodiments, particles comprising the Montelukast in the emulsion have D90 of less than about 50 µm and greater than 8 µm, and a D50 of less than about 30 µm and greater than about 5 µm. In some embodiments, particles comprising the Montelukast in the emulsion have D90 of about 5 µm to 50 µm and a D50 of 2 µm to 30 µm, D90 of about 10 µm to 40 µm and a D50 of about 3 µm to 25 µm, D90 of about 10 µm to 30 µm and a D50 of about 3 µm to 20 µm, D90 of about 10 µm to 20 µm and a D50 of about 5 µm to 10 µm. In some embodiments, the particles comprising the Montelukast in the emulsion have D90 of about 10 µm to 14 µm and a D50 of 7 µm to 11 µm, In some embodiments, particles comprising the Montelukast in the emulsion have D10 of less than about 20 µm, less than about 15 µm, less than about 12 µm, less than about 10 µm, or less than about 7 µm. In some embodiments, particles comprising the Montelukast in the emulsion have D10 of less than about 7 µm. In some embodiments, particles comprising the Montelukast in the emulsion have D10 greater than about 1 greater than about 2 greater than about 3 greater than about 4 greater than about 5 greater than about 6 In some embodiments, particles comprising the Montelukast in the emulsion have D10 of greater than about 3 µm.

In some embodiments, particles comprising the Montelukast in the emulsion have a particle size distribution as found in Table 1:

TABLE 1

| D90 (µm) | D50 (µm) | D10 (µm) |
|---|---|---|
| <50 | <30 | <15 |
| 5-50 | 2-30 | 1-15 |
| 5-40 | 2-25 | 1-15 |
| 5-30 | 2-20 | 1-15 |
| 10-25 | 4-20 | 1-15 |
| 10-20 | 5-15 | 1-10 |

The particles comprising Montelukast are physically stable in the topical emulsion over an extended period of time. The term "physically stable" can refer to particles that remain homogenously dispersed in the topical emulsion for an extended period of time, i.e., the particles do not precipitate. Likewise, the term "physically stable" can refer to particles that remain homogenously dispersed in the topical emulsion for an extended period of time, i.e., the particles do not form aggregates in the emulsion. The term "physically stable" can also refer to topical emulsion in which no phase separation is identified for an extended period of time.

Additionally, the term "physically stable" can refer to particles that remain the same size distribution in the topical emulsion for an extended period of time, i.e., the particles do not further crystalize, agglomerate, dissolve, or otherwise break apart in the emulsion. For example, in some embodiments, the D50 does not change greater than 20%, greater than 15%, greater than 10%, greater than 5%, greater than 2%, or greater than 1% over an extended period of time. In some embodiments, the D90 does not change greater than 20%, greater than 15%, greater than 10%, greater than 5%, greater than 2%, or greater than 1% over an extended period of time. In some embodiments, the average particle size of the particles does not change greater than 20%, greater than 15%, greater than 10%, greater than 5%, greater than 2%, or greater than 1% over an extended period of time.

In some embodiments, the particles comprising Montelukast are physically stable an "extended period of time." One skilled in the art can appreciate the benefits of a topical emulsion that is stable during manufacturing, transport and storage of the topical emulsion before use. In some embodiments, extended period of time can include for at least one week, at least two weeks, at least three weeks, at least one month, at least two months, three months, at least four months, at least six months, at least one year or at least two years.

The skilled artisan can appreciate that physical stability can be affected by several factors, e.g., temperature, humidity, oxidation, sunlight, etc. As used herein, physical stability is determined using standard conditions or accelerated conditions in a sealed container not subject to light degradation or oxidation.

In some embodiments, the particle size of particles in the emulsion comprising Montelukast in the emulsion does not change greater than 20% over a period of three months at 25° C., six months at 25° C., nine months at 25° C., or one year at 25° C. In some embodiments, the particle size in the emulsion does not change greater than 10% over a period of three months at 25° C., six months at 25° C., nine months at 25° C., or one year at 25° C. In some embodiments, the particle size in the emulsion does not change greater than 5% over a period of three months at 25° C., six months at 25° C., nine months at 25° C., or one year at 25° C. In some embodiments, the particle size in the emulsion does not change greater than 1% over a period of three months at 25° C., six months at 25° C., nine months at 25° C., or one year at 25° C.

In some embodiments, the particle size of particles comprising Montelukast in the emulsion does not change greater than 20% over a period of three months at 37° C., six months at 37° C., nine months at 37° C., or one year at 37° C. In some embodiments, the particle size in the emulsion does not change greater than 10% over a period of three months at 37° C., six months at 37° C., nine months at 37° C., or one year at 37° C. In some embodiments, the particle size in the emulsion does not change greater than 5% over a period of three months at 37° C., six months at 37° C., nine months at 37° C., or one year at 37° C. In some embodiments, the particle size in the emulsion does not change greater than 1% over a period of three months at 37° C., six months at 37° C., nine months at 37° C., or one year at 37° C.

The Montelukast particles can be formed by various methods. In some embodiments, the particles are formed in-situ in the emulsions. Alternatively, in some embodiments, the particles of Montelukast or pharmaceutically acceptable salt thereof are obtained by milling, screening, or other methods known in the art. Methods of determining particle size are known to the skilled artisan and can include particle size analyzer, light microscopy, and/or electron microscopy.

One of skill in the art can appreciate the in-situ formation of particles comprising Montelukast. In some embodiments, greater than 50% of the Montelukast in the emulsion is in particles, with the remaining less than 50% being in solution. In some embodiments, greater than 55%, greater than 65%, greater than 70%, greater than 75%, greater than 80% or greater than 85% of the Montelukast in the emulsion is in particles. In some embodiments, about 70% to about 95% of the Montelukast in the emulsion is in particles, with the remaining 5% to 30% being in solution. In some embodiments, about 80% to about 95% of the Montelukast in the emulsion is in particles, with the remaining 5% to 20% being in solution.

In some embodiments, the Montelukast or pharmaceutically acceptable salt thereof is chemically stable in the emulsion. The term "chemically stable" indicates the Montelukast does not appreciably degrade to form impurities. Various degradation impurities are known in the art, and include
1. a sulfoxide impurity: 1-[((RS)[1-[3-[(E)-2-(7-Chloroquinolin-2-yl)ethenyl)phenyl)-3-[2-(1-hydroxy-1-methylethyl)phenyl)propyl]sylfinyl]methyl]clycloropyl]acetic acid;
2. a diol impurity: 2-(2-(3-(S)-(3(E)-(2-(7-Chloro-2-quinolinyl)-ethenyl)phenyl)-3-hydroxypropyl)phenyl)-2-propanol;
3. a methyl styrene impurity: [1-[[[(1R)-1-3-[(E)-(7-Chloroquinolin-2-yl)ethenyl]phenyl]-3-[2-(1-methylethenyl)phenyl]propyl]sulfanyl]methyl]cyclopropyl]acetic acid (USP imp F);
4. a cis-isomer impurity: [1-[[[(1R)-1-[3-[(Z)-2-(7-Chloroquinolin-2-yl)ethenyl]phenyl]-3-[2-(1-hydroxy-1-methylethyl)phenyl]propyl]sulfanyl]methyl]cyclopropyl]acetic acid;
5. a Michael adduct impurity (1): 1-[[[((1R)-1-[3-[(1R)-1-[[[1-(Carboxymethyl) cyclopropyl]methyl]sulfanyl]-2-(7-chloroquinolin-2-yl)ethyl]phenyl]-3-[2-(1-hydroxy-1-methylethyl)phenyl]propyl]sulfonyl]methyl]cyclopropyl] acetic acid;
6. a Michael adduct impurity (2): 1-[[[((1R)-1-[3-[(1S)-1-[[[1-(Carboxymethyl) cyclopropyl]methyl]sulfanyl]-2-(7-chloroquinolin-2-yl)ethyl]phenyl]-3-[2-(1-hydroxy-1-methylethyl)phenyl]propyl]sulfonyl]methyl]cyclopropyl] acetic acid;
7. a methyl ketone impurity: [1-({((1R)-3-(2-acetylphenyl)-1-[3-[ϵ-2-(7-chloroquinolin-2-yl)ethenyl)phenyl]propyl]sulfanyl]methyl]cyclopropyl]acetic acid;

As used herein, the term "total impurities" refers to the combined amount of a sulfoxide impurity, a methyl styrene impurity, and a cis-isomer impurity, as well as all other degradation impurities found in the topical emulsion. In some embodiments, the total impurities in the emulsion are less than 2% after 3 months at 25° C. In some embodiments, the total impurities in the emulsion are less than 1% after 3 months at 25° C. In some embodiments, the total impurities in the emulsion are less than 0.5% after 3 months at 25° C. In some embodiments, the sulfoxide impurity in the emulsion is less than 2% after 3 months at 25° C. In some embodiments, the sulfoxide impurity in the emulsion is less than 1% after 3 months at 25° C. In some embodiments, the sulfoxide impurity in the emulsion is less than 0.5% after 3 months at 25° C. In some embodiments, the cis-isomer impurity in the emulsion is less than 1% after 3 months at 25° C. In some embodiments, the cis-isomer impurity in the emulsion is less than 0.5% after 3 months at 25° C. In some embodiments, the cis-isomer impurity in the emulsion is less than 0.1% after 3 months at 25° C. In some embodiments, the methylstyrene impurity in the emulsion is less than 0.2% after 3 months at 25° C. Methods of determining impurities are well established, and can include conventional techniques such as HPLC.

The impurities can be measured after a designated period of time at standard room temperature (RT) conditions (25° C., 60% humidity), intermediate (INT) conditions (30° C., 65% humidity), and/or accelerated (ACC) conditions (40° C., 75% humidity).

In some embodiments, the total impurities in the emulsion are less than 2% after 6 months or 1 year at 25° C. In some embodiments, the total impurities in the emulsion are less than 1% after 6 months or 1 year at 25° C. In some embodiments, the total impurities in the emulsion are less than 0.5% after 6 months or 1 year at 25° C. In some embodiments, the sulfoxide impurity in the emulsion is less than 2% after 6 months or 1 year at 25° C. In some embodiments, the sulfoxide impurity in the emulsion is less than 1% after 6 months or 1 year at 25° C. In some embodiments, the sulfoxide impurity in the emulsion is less than 0.5% after 6 months or 1 year at 25° C. In some embodiments, the cis-isomer impurity in the emulsion is less than 1% after 6 months or 1 year at 25° C. In some embodiments, the cis-isomer impurity in the emulsion is less than 0.1% after 6 months or 1 year at 25° C. In some embodiments, the cis-isomer impurity in the emulsion is less than 0.05% after 6 months or 1 year at 25° C. In some embodiments, the methylstyrene impurity in the emulsion is less than 0.2% after 6 months or 1 year at 25° C. In some embodiments, the methylstyrene impurity in the emulsion is less than 0.1% after 6 months or 1 year at 25° C.

In some embodiments, the total impurities in the emulsion are less than 2% after 3 months at 30° C. In some embodiments, the total impurities in the emulsion are less than 1% after 3 months at 30° C. In some embodiments, the total impurities in the emulsion are less than 0.5% after 3 months at 30° C. In some embodiments, the sulfoxide impurity in the emulsion is less than 2% after 3 months at 30° C. In some embodiments, the sulfoxide impurity in the emulsion is less than 1% after 3 months at 30° C. In some embodiments, the sulfoxide impurity in the emulsion is less than 0.5% after 3 months at 30° C. In some embodiments, the cis-isomer impurity in the emulsion is less than 1% after 3 months at 30° C. In some embodiments, the cis-isomer impurity in the emulsion is less than 0.1% after 3 months at 30° C. In some embodiments, the methylstyrene impurity in the emulsion is less than 0.2% after 3 months at 30° C.

In some embodiments, the total impurities in the emulsion are less than 2% after 6 months or 1 year at 30° C. In some embodiments, the total impurities in the emulsion are less than 1% after 6 months or 1 year at 30° C. In some embodiments, the total impurities in the emulsion are less than 0.5% after 6 months or 1 year at 30° C. In some embodiments, the sulfoxide impurity in the emulsion is less than 2% after 6 months or 1 year at 30° C. In some embodiments, the sulfoxide impurity in the emulsion is less than 1% after 6 months or 1 year at 30° C. In some embodiments, the sulfoxide impurity in the emulsion is less than 0.5% after 6 months or 1 year at 30° C. In some embodiments, the cis-isomer impurity in the emulsion is less than 1% after 6 months or 1 year at 30° C. In some embodiments, the cis-isomer impurity in the emulsion is less than 0.1% after 6 months or 1 year at 30° C. In some embodiments, the methylstyrene impurity in the emulsion is less than 0.2% after 6 months or 1 year at 30° C.

In some embodiments, the total impurities in the emulsion are less than 2% after 3 months under accelerated conditions. In some embodiments, the total impurities in the emulsion are less than 1% after 3 months under accelerated conditions. In some embodiments, the total impurities in the emulsion are less than 0.5% after 3 months under accelerated conditions. In some embodiments, the sulfoxide impurity in the emulsion is less than 2% after 3 months under accelerated conditions. In some embodiments, the sulfoxide impurity in the emulsion is less than 1% after 3 months under accelerated conditions. In some embodiments, the sulfoxide impurity in the emulsion is less than 0.5% after 3 months under accelerated conditions. In some embodiments, the cis-isomer impurity in the emulsion is less than 1% after 3 months under accelerated conditions. In some embodiments, the cis-isomer impurity in the emulsion is less than 0.1% after 3 months under accelerated conditions. In some embodiments, the methylstyrene impurity in the emulsion is less than 0.2% after 3 months under accelerated conditions.

In some embodiments, the total impurities in the emulsion are less than 2% after 6 months or 1 year under accelerated conditions. In some embodiments, the total impurities in the emulsion are less than 1% after 6 months or 1 year under accelerated conditions. In some embodiments, the total impurities in the emulsion are less than 0.5% after 6 months or 1 year under accelerated conditions. In some embodiments, the sulfoxide impurity in the emulsion is less than 2% after 6 months or 1 year under accelerated conditions. In some embodiments, the sulfoxide impurity in the emulsion is less than 1% after 6 months or 1 year under accelerated conditions. In some embodiments, the sulfoxide impurity in the emulsion is less than 0.5% after 6 months or 1 year under accelerated conditions. In some embodiments, the cis-isomer impurity in the emulsion is less than 1% after 6 months or 1 year under accelerated conditions. In some embodiments, the cis-isomer impurity in the emulsion is less than 0.1% after 6 months or 1 year under accelerated conditions. In some embodiments, the methylstyrene impurity in the emulsion is less than 0.2% after 6 months or 1 year under accelerated conditions.

The Montelukast of the emulsion of present disclosure can be in an amorphous form, or a crystalline form. In some embodiments, the Montelukast in the particles in the emulsion is in a polymorphic crystalline form. For example, in some embodiments, the Montelukast is Montelukast acid Form I as described in US 2005/0187243, incorporated herein in its entirety.

The topical emulsion as described herein comprises (a) Montelukast or pharmaceutically acceptable salt thereof, and (b) a carbomer at specified percentages. As used throughout, a percentage, i.e., "%", of a component of the emulsion refers to the weight percent, i.e., w/w.

The topical emulsions provided herein can comprise various concentration of Montelukast or pharmaceutically acceptable salt thereof. In some embodiments, the topical emulsion comprises about 0.05% to about 20%, about 1% to about 15%, about 2% to about 12%, about 3% to about 10%, about 4% to about 8%, about 5% to about 7% or about 6% Montelukast or pharmaceutically acceptable salt thereof. In some embodiments, the topical emulsion comprises about 3% to about 8% Montelukast or pharmaceutically acceptable salt thereof.

The topical emulsions provided herein can comprise various concentration of carbomer. In some embodiments, the topical emulsion comprises about 0.4% to about 5% carbomer, about 0.5% to about 4% carbomer, about 0.8% to about 3% carbomer, or about 1% to about 2% carbomer. While not being bound by any particular theory, in some embodiments the carbomer can lower the pH of the emulsion to provide the free acid form of Montelukast, which can increase penetration of the Montelukast into the skin.

Various carbomers are known in the art. The term carbomer refers to synthetic high-molecular weight polymers primarily made from acrylic acid. Carbomers may be homopolymers of acrylic acid, or copolymers with acrylic acid and $C_{10}$-$C_{30}$ alkyl acrylate crosslinked with allyl ether of pentaerythritol, allyl ether of sucrose, or allyl ether of propylene. Carbomer homopolymers can comprise acrylic acid crosslinked with allyl sucrose or allyl pentaerythritol. Carbomer codes (e.g., 910, 934, 940, 941, and 934P) are an indication of molecular weight and the specific components of the polymer. One tradename for carbomers is CARBOPOL® (Lubrizol Corporation, Wickliffe, OH).

Suitable carbomers can include, but are not limited to, the commercially available carbomers in Table 2, manufactured by Lubrizol Corporation.

TABLE 2

| Carbopol ® Polymer | Polymerization Solvent | Carbomer Product Type | Viscosity, cP (0.5 wt % at pH 7.5) |
|---|---|---|---|
| 71G NF | Ethyl Acetate | Homopolymer | 4,000-11,000 |
| 971P NF | Ethyl Acetate | Homopolymer | 4,000-11,000 |
| 974P NF | Ethyl Acetate | Homopolymer | 29,400-39,400 |
| 980 NF | Cosolvent[1] | Homopolymer | 40,000-60,000 |
| 981 NF | Cosolvent[1] | Homopolymer | 4,000-10,000 |
| 5984 EP | C5984 EPosolvent[1] | Homopolymer | 30,500-39,400 |
| ETD 2020 NF | Cosolvent[1] | Interpolymer | 47,000-77,0002 |
| Ultrez 10 NF | Cosolvent[1] | Interpolymer | 45,000-65,000 |
| 934 NF | Benzene | Homopolymer | 30,500-39,400 |
| 934P NF | Benzene | Homopolymer | 29,400-39,400 |
| 940 NF | Benzene | Homopolymer | 40,000-60,000 |
| 941 NF | Benzene | Homopolymer | 4,000-10,000 |
| 1342 NF | Benzene | Copolymer | 9,500-26,5002 |

[1]Cosolvent system made using cyclohexane and ethyl acetate
Carbopol homopolymers are polymers of acrylic acid crosslinked with allyl sucrose or allyl pentaerythritol
Carbopol copolymers are polymers of acrylic acid and C10-C30 alkyl acrylate crosslinked with allyl pentaerythritol
Carbopol interpolymers are a carbomer homopolymer or copolymer that contains a block copolymer of polyethylene glycol and a long chain alkyl acid ester In some embodiments, the carbomer is Carbopol® 974P NF, Carbopol® 934P NF, Carbopol® 971P NF, Carbopol® 934 NF. In some embodiments, the carbomer is Carbopol® 974P NF. (Homopolymer Type B, NF).

In some embodiments, the carbomer is a Carbopol®. In some embodiments, the topical emulsion comprises about 0.4% to about 5% Carbopol®, about 0.5% to about 4% Carbopol®, about 0.8% to about 3% Carbopol®, or about 1% to about 2% Carbopol®.

In some embodiments, the topical emulsion comprises water. In some embodiments, the water is about 30% to about 80%, about 40% to about 70%, about 45% to about 65%, or about 50% to 60% of the emulsion.

The pH of the topical emulsion can be about 3.0 to about 6.5, about 3.5 to about 6.5, about 3.5 to about 6.0, or about 4 to about 6. At this pH range, some or all of the Montelukast can be in its free acid form. In some embodiments, the pH of the topical emulsion can be between about 3.0 to about 6.0, about 4.5 to about 6, about 4 to about 5.5, about 4.5 to about 5.5, or about 5 to about 6. Various means of adjusting the pH are known in the art, and can include the additional of acids or bases to achieve the desired pH. In some embodiments, a strong acid, e.g., hydrochloric acid, is not used to adjust the pH of the emulsion.

In some embodiments, the topical emulsion can comprise a penetration enhancer. Suitable penetration enhances are known in the art and can be used with the present invention. Some examples of penetration enhancers include, but are not limited to, polyols and esters, including polyethylene glycol, polyethylene glycol monolaurate, and butanediol; sulfoxides, including dimethylsulfoxide (DMSO) and decylmethylsulfoxide; ethers, including diethylene glycol monoethyl ether (e.g., Transcutol®P) and diethylene glycol monomethyl ether; fatty acids, including lauric acid, oleic acid, and valeric acid; fatty acid esters, including isopropyl myristate, isopropyl palmitate, methyl propionate, and ethyl oleate; nitrogenous compounds including urea, dimethyl acetamide, dimethylformamide 2-pyrrolidone, ethanolamine, methyl-2-pyrrolidone, diethanolamine, and triethanolamine; terpenes; alkanones; organic acids, including salicylic acid, citric acid, and succinic acid; and any mixtures thereof.

Various concentrations of penetration enhancers can be used. In some embodiments, the penetration enhancer is about 0.01% to about 10%, about 0.1% to about 10%, about 1% to about 10% or about 2% to about 8% of the emulsion.

In some embodiments, the penetration enhancer is DMSO. In some embodiments, the amount of DMSO in the topical emulsion is limited, as DMSO in some instances can cause irritation to the skin. Thus, in some embodiments, the topical emulsion comprises less than 5% DMSO or less than 3% DMSO.

In some instances, the topical emulsion comprises an alcohol. In some embodiments, the alcohol can cause irritation when applied to the skin, e.g., in some embodiments with $C_1$-$C_5$ alcohol. Thus, in some embodiments, the topical emulsion comprises less than 20% alcohol, less than 15% alcohol, less than 10% alcohol, or less than 5% alcohol. In some embodiments, the topical emulsion comprises less than 20% $C_1$-$C_5$ alcohol, less than 15% $C_1$-$C_5$ alcohol, less than 10% $C_1$-$C_5$ alcohol, less than 5% $C_1$-$C_5$ alcohol, less than 2% $C_1$-$C_5$ alcohol, less than 1% $C_1$-$C_5$ or no $C_1$-$C_5$ alcohol. In some embodiments, the $C_1$-$C_5$ alcohol can refer to methanol, ethanol, propanol, iso-propanol, butanol, iso-butanol, or pentanol, etc.

In some embodiments, the topical emulsion further comprises a preservative, an amphiphilic compound, an emulsifier, a lubricant, or combinations thereof.

In some embodiments, the preservative can be an antioxidant. In some embodiments, the antioxidant is butylated hydroxy anisole (BHA), butylated hydroxy toluene (BHT), or combinations thereof. In some embodiments, the preservative can include a paraben such as a methyl paraben or propyl paraben. The preservative can be about 0.01% to about 10% by weight, about 0.05% to about 5% by weight, about 0.1% to about 1% by weight, about 0.1% to about 0.5% by weight, of the topical emulsion.

In some embodiments, the topical emulsion comprises an amphiphilic compound. In some embodiments, the amphiphilic compound comprises oleyl alcohol, polyoxyglycerides, propylene carbonate, propylene glycol, or combinations thereof. In some embodiments, the amphiphilic compound is propylene glycol.

Various concentrations of amphiphilic compounds can be in the topical formulation. In some embodiments, the amphiphilic compound is about 1% to about 30%, about 2% to about 25%, about 5% to about 25%, or about 10% to about 20% of the topical emulsion. In some embodiments, the amphiphilic compound is propylene glycol, and the propylene glycol is about 1% to about 30%, about 2% to about 25%, about 5% to about 25%, or about 10% to about 20% of the topical emulsion.

In some embodiments, the topical emulsion comprises an emulsifier. Suitable emulsifiers for dermatological applications are known in the art. In some embodiments, the emulsifier can be Poloxamer188/polysorbate 20, Silicone Glycerol, polysorbate (e.g., polysorbate 20, polysorbate 40, polysorbate 60 or polysorbate 80). In some embodiments, the emulsifier is a polysorbate. In some embodiments, the emulsifier is a polysorbate 80. In some embodiments, the emulsifier is a polysorbate 60. In some embodiments, the emulsifier is a polysorbate 40.

In some embodiments, the emulsifier is about 0.01% to about 15%, about 0.05% to about 10%, about 0.1% to about 10%, or about 1% to about 5% of the topical emulsion. In some embodiments, the emulsifier is a polysorbate, and the polysorbate is about 0.01% to about 15%, about 0.05% to about 10%, about 0.1% to about 10%, or about 1% to about 5% of the topical emulsion.

In some embodiments, the topical emulsion comprises a lubricant. Suitable lubricants for dermatological applications are known in the art. In some embodiments, the lubricant can include polypropylene glycol (PPG) stearyl ether, Sodium Hyaluronate, Cyclomethicone and Dimethicone 5225C, Cyclomethicone, polypropylene glycol-15 stearyl ether, or combinations thereof. In some embodiments, the lubricant can include polypropylene glycol (PPG) stearyl ether, e.g., PPG-15 stearyl ether.

In some embodiments, the emulsions comprising a carbomer as provided herein have a smaller globule size relative to previous Montelukast formulations. While not being bound by any theory, in some embodiments, emulsions comprising a smaller globule size are more stable relative to emulsions comprising a larger globule size. For example, in some embodiments, the smaller globule size may contribute to the physical stability of products, e.g., Montelukast. See, e.g., Mohsin et al., *Tropical J. Pharma. Research*, 15(6): 1115-1121 (2016). In some embodiments, a small globule size prevents the globule coalescence and sedimentation against gravitational force.

Thus, in some embodiments, the disclosure provides a method of stabilizing a Montelukast formulation, comprising adding a carbomer to the formulation in an amount sufficient to decrease the globule size to less than about 200 μm, less than about 100 μm, less than about 50 μm, less than about 25 μm or less than about 20 μm.

As used herein, determinations of globule size are as described in the Example section herein. One of skill in the art will appreciate that globule size in a single emulsion sample can vary. Thus, in some embodiments, any reference to globule size can include a "maximum globule size," i.e., the size of the largest globule measured in the microscope field of view for an emulsion sample. In some embodiments, the maximum globule size is the size of the largest globule measured in one microscopic field, or two or more microscopic fields, e.g., three, four, five, six, seven, eight, nine or ten microscopic fields in an emulsion sample. In some embodiments, the term maximum globule size can refer to the average of the largest globule measured in two or more microscopic fields, e.g., three, four, five, six, seven, eight, nine or ten microscopic fields in an emulsion sample.

In some embodiments, the emulsion has a maximum globule size of less than about 200 less than about 150 less than about 100 less than about 75 less than about 50 less than about 25 or less than about 20 In some embodiments, the emulsion has a maximum globule size of about 1 μm to about 100 about 1 μm to about 50 about 1 μm to about 25 μm or about 1 μm to about 20 In some embodiments, the emulsion has a maximum globule size of about 1 μm to about 15 about 2 μm to about 12 about 3 μm to about 10 or about 5 μm to about 10 μm.

Topical Gel

The present disclosure provides for a topical gel comprising Montelukast or pharmaceutically acceptable salt thereof. The present disclosure provides a gel in which Montelukast or any salt thereof, with a molecular weight of about 600 g/mol, is able to achieve skin penetration in an amount to be therapeutically effective, without the use of solvents, such as $C_1$-$C_5$ alcohols, that are known to irritate the skin. The present disclosure provides a topical gel suitable for application to the skin without undue irritation, while maintaining the physical stability, chemical stability and efficacy of the Montelukast.

In some embodiments, the disclosure provides for a topical gel comprising Montelukast or pharmaceutically acceptable salt thereof having little or no water present. Applicant has found a topical gel in which the Montelukast remains stable over an extended period of time, while still allowing for topical penetration of Montelukast within the skin. The present disclosure also provides for a topical gel formulation with little or no water in which the Montelukast does not precipitate when stored for an extended period of time.

In some embodiments, the disclosure provides for a topical gel comprising (a) about 0.5% to about 10% Montelukast or pharmaceutically acceptable salt thereof; (b) about 0.2% to about 8% cellulose polymer; and (c) about 80% to about 95% amphiphilic compound; wherein the gel comprises less than 4% water.

The topical gel as described herein comprises (a) Montelukast or pharmaceutically acceptable salt thereof, and (b) a cellulose polymer, and (c) an amphiphilic compound at specified percentages. As used throughout, a percentage, i.e., "%", of a component of the gel refers to the weight percent, i.e., w/w.

The topical gel provided herein can comprise various concentration of Montelukast or pharmaceutically acceptable salt thereof. In some embodiments, the topical gel comprises about 0.05% to about 20%, about 1% to about 15%, about 2% to about 12%, about 3% to about 10%, about 4% to about 8%, about 5% to about 7% or about 6% Montelukast or pharmaceutically acceptable salt thereof. In some embodiments, the topical gel comprises about 3% to about 8% Montelukast or pharmaceutically acceptable salt thereof.

In some instances, the topical gel comprises little or no alcohol. In some embodiments, the alcohol can cause irritation when applied to the skin, e.g., in some embodiments with $C_1$-$C_5$ alcohol. Thus, in some embodiments, the topical gel comprises less than 10% alcohol, less than 5% alcohol, less than 2% alcohol, or less than 1% alcohol or no alcohol, i.e., alcohol free. In some embodiments, the topical gel comprises less than 10% $C_1$-$C_5$ alcohol, less than 5% $C_1$-$C_5$ alcohol, less than 2% $C_1$-$C_5$ alcohol, less than 1% $C_1$-$C_5$ alcohol, less than 0.5% $C_1$-$C_5$ alcohol, less than 0.1% $C_1$-$C_5$ or no $C_1$-$C_5$ alcohol. In some embodiments, the topical gel comprises no $C_1$-$C_5$ alcohol. In some embodiments, the $C_1$-$C_5$ alcohol can refer to methanol, ethanol, propanol, iso-propanol, butanol, iso-butanol, or pentanol, etc.

The present disclosure provides for a topical Montelukast gel that is substantially free of water. In some embodiments, a gel comprising reduced amounts of water can provide increased stability of the gel and the Montelukast, providing for longer storage times. In some embodiments, the topical gel comprises less than 2% water. In some embodiments, the gel comprises less than 1% water. In some embodiments, the gel is anhydrous.

In some embodiments, the topical gel provided herein does not comprise a preservative. Applicant found that the gel formulations as disclosed was chemically stable even in the absent of a preservative. Additionally, the presence of a preservative, such as an antioxidant BHA, propyl gallate, alpha tocopherol, ascorbic acid, and their combinations unexpectedly caused increased degradation of Montelukast.

Thus, in some embodiments, the disclosure provides a topical gel, wherein the gel does not comprise a preservative, or a highly reduced amount of preservative. In some embodiments, the disclosure provides a topical gel, wherein the gel does not comprise a BHA, propyl gallate, alpha tocopherol, ascorbic acid, and their combinations, or a highly reduced amount of BHA, propyl gallate, alpha tocopherol, ascorbic acid, and their combinations.

The present disclosure provides for a topical gel comprising Montelukast and a cellulose polymer. Cellulose polymers suitable for the topical gel disclosed herein include, but are not limited to, ethyl cellulose, methyl cellulose, propyl cellulose, butyl cellulose, hydroxymethyl cellulose, hydroxyethyl cellulose, hydroxypropyl cellulose, hydroxybutyl cellulose, hydroxymethyl propyl cellulose, hydroxyethyl propyl cellulose, hydroxypropyl methyl cellulose, or hydroxypropyl ethyl cellulose. Various derivatives of cellulose polymers are known in the art, and can comprise different average number of substituted hydroxyl groups per glucose unit, referred to as the degree of substitution (DS). Complete substitution would provide a DS of 3. Because the hydroxypropyl group added contains a hydroxyl group, this can also be etherified during preparation of HPC. When this occurs, the number of moles of hydroxypropyl groups per glucose ring, moles of substitution (MS), can be higher than 3.

Because cellulose can be crystalline, cellulose polymers comprising hydroxyl groups generally have an MS about 4 in order to reach a good solubility in water. Cellulose polymers can comprise a combination of hydrophobic and hydrophilic groups, so they have a lower critical solution temperature (LCST), e.g., at 45° C. In some embodiments, at temperatures below the LCST, the cellulose polymer is readily soluble in water; above the LCST, cellulose is not soluble. In some embodiments, the cellulose polymers have a LCST suitable for dermatological use.

In some embodiments, the cellulose polymer comprises hydroxyethylcellulose and hydroxypropyl methylcellulose. In some embodiments, the cellulose polymer is hydroxypropyl methylcellulose. In some embodiments, the cellulose polymer is hydroxypropylcellulose.

Various amounts of cellulose polymers can be used in the topical gels of the present disclosure. In some embodiments, the topical gel comprises less than about 15%, less than about 10%, less than about 8%, or less than about 6% cellulose polymer. In some embodiments, the topical gel comprises about 0.5% to about 15%, about 0.5% to about 10%, about 0.5% to about 8%, or about 0.5% to about 6% cellulose polymer. In some embodiments, the topical gel comprises about 1% to about 10%, about 2% to about 6%, or about 3% to about 4% cellulose polymer.

In some embodiments, the cellulose polymer is ethyl cellulose or hydroxypropyl cellulose, wherein the topical gel comprises less than about 15%, less than about 10%, less than about 8%, or less than about 6% ethyl cellulose or hydroxypropyl cellulose. In some embodiments, the topical gel comprises about 0.5% to about 15%, about 0.5% to about 10%, about 0.5% to about 8%, or about 0.5% to about 6% ethyl cellulose or hydroxypropyl cellulose. In some embodiments, the topical gel comprises about 1% to about 10%, about 2% to about 6%, or about 3% to about 4% ethyl cellulose or hydroxypropyl cellulose. In some embodiments, the topical gel comprises about 2% to about 6% ethyl cellulose or hydroxypropyl cellulose.

In some embodiments, the topical gel comprises an amphiphilic compound. In some embodiments, the amphiphilic compound in the topical gel comprises oleyl alcohol, polyoxyglycerides, propylene carbonate, propylene glycol, or combinations thereof. In some embodiments, the amphiphilic compound in the topical gel is propylene glycol.

Various concentrations of amphiphilic compounds can be used with the topical gel. In some embodiments, the amphiphilic compound in the topical gel is about 60% to about 98%, about 70% to about 96%, about 75% to about 95%, or about 80% to about 95% of the topical gel. In some embodiments, the amphiphilic compound in the topical gel is about 85% to about 95% of the topical gel. In some embodiments, the amphiphilic compound in the topical gel is propylene glycol, and the propylene glycol is about 60% to about 98%, about 70% to about 96%, about 75% to about 95%, about 80% to about 95% or about 85% to about 95% of the topical gel.

Applicant has found that the topical gel described in the present disclosure provides for a chemically stable formulation, wherein the topical gel has reduced impurities over an extended period of time. The term "chemically stable" indicates the Montelukast does not appreciably degrade to form impurities in the topical gel. Various degradation impurities are known in the art, and include (a) a sulfoxide impurity, (b) a diol impurity, (c) a methyl styrene impurity, (d) a cis-isomer impurity. (e) a Michael adduct impurity (1), (f) a Michael adduct impurity (2), and (g) a methyl ketone impurity.

As used herein, the term "total impurities" refers to the combined amount of a sulfoxide impurity, a methyl styrene impurity, and a cis-isomer impurity and other degradation impurities found in the topical gel. In some embodiments, the total impurities in the gel are less than 2% after 3 months at 25° C. In some embodiments, the total impurities in the gel are less than 1% after 3 months at 25° C. In some embodiments, the total impurities in the gel are less than 0.5% after 3 months at 25° C. In some embodiments, the sulfoxide impurity in the gel is less than 2% after 3 months at 25° C. In some embodiments, the sulfoxide impurity in the gel is less than 1% after 3 months at 25° C. In some embodiments, the sulfoxide impurity in the gel is less than 0.5% after 3 months at 25° C. In some embodiments, the cis-isomer impurity in the gel is less than 1% after 3 months at 25° C. In some embodiments, the cis-isomer impurity in the gel is less than 0.1% after 3 months at 25° C. In some embodiments, the methylstyrene impurity in the gel is less than 0.2% after 3 months at 25° C.

In some embodiments, the total impurities in the gel are less than 2% after 6 months or 1 year at 25° C. In some embodiments, the total impurities in the gel are less than 1% after 6 months or 1 year at 25° C. In some embodiments, the total impurities in the gel are less than 0.5% after 6 months or 1 year at 25° C. In some embodiments, the sulfoxide impurity in the gel is less than 2% after 6 months or 1 year at 25° C. In some embodiments, the sulfoxide impurity in the gel is less than 1% after 6 months or 1 year at 25° C. In some embodiments, the sulfoxide impurity in the gel is less than 0.5% after 6 months or 1 year at 25° C. In some embodiments, the cis-isomer impurity in the gel is less than 1% after 6 months or 1 year at 25° C. In some embodiments, the cis-isomer impurity in the gel is less than 0.1% after 6 months or 1 year at 25° C. In some embodiments, the cis-isomer impurity in the gel is less than 0.05% after 6 months or 1 year at 25° C. In some embodiments, the methylstyrene impurity in the gel is less than 0.2% after 6 months or 1 year at 25° C. In some embodiments, the methylstyrene impurity in the gel is less than 0.1% after 6 months or 1 year at 25° C.

In some embodiments, the total impurities in the gel are less than 2% after 3 months at 37° C. In some embodiments, the total impurities in the gel are less than 1% after 3 months at 37° C. In some embodiments, the total impurities in the gel are less than 0.5% after 3 months at 37° C. In some embodiments, the sulfoxide impurity in the gel is less than 2% after 3 months at 37° C. In some embodiments, the sulfoxide impurity in the gel is less than 1% after 3 months at 37° C. In some embodiments, the sulfoxide impurity in the gel is less than 0.5% after 3 months at 37° C. In some embodiments, the cis-isomer impurity in the gel is less than 1% after 3 months at 37° C. In some embodiments, the cis-isomer impurity in the gel is less than 0.1% after 3 months at 37° C. In some embodiments, the methylstyrene impurity in the gel is less than 0.2% after 3 months at 37° C.

In some embodiments, the total impurities in the gel are less than 2% after 6 months or 1 year at 37° C. In some embodiments, the total impurities in the gel are less than 1% after 6 months or 1 year at 37° C. In some embodiments, the total impurities in the gel are less than 0.5% after 6 months or 1 year at 37° C. In some embodiments, the sulfoxide impurity in the gel is less than 2% after 6 months or 1 year at 37° C. In some embodiments, the sulfoxide impurity in the gel is less than 1% after 6 months or 1 year at 37° C. In some embodiments, the sulfoxide impurity in the gel is less than 0.5% after 6 months or 1 year at 37° C. In some embodiments, the cis-isomer impurity in the gel is less than 1% after 6 months or 1 year at 37° C. In some embodiments, the cis-isomer impurity in the gel is less than 0.1% after 6 months or 1 year at 37° C. In some embodiments, the methylstyrene impurity in the gel is less than 0.2% after 6 months or 1 year at 37° C.

Stable Topical Formulations

The disclosure herein provides for formulations that are both physically and chemically stable as described previously. In some embodiments, the disclosure provides a stable topical formulation comprising about 0.5% to about 10% Montelukast or pharmaceutically acceptable salt thereof; wherein the total impurities resulting from the degradation of Montelukast in the composition are less than 2% after 12, 24 or 36 months at 25° C. and 60% humidity. In some embodiments, a sulfoxide impurity in the stable topical formulation is less than 2% after 12, 24 or 36 months at 25° C. and 60% humidity. In some embodiments, a cis-isomer impurity in the stable topical formulation is less than 1% after 12, 24 or 36 months at 25° C. and 60% humidity.

In some embodiments, a methylstyrene impurity in the stable topical formulation is less than 0.2% after 12, 24 or 36 months at 25° C. and 60% humidity.

In some embodiments, the disclosure provides a stable topical formulation comprising about 0.5% to about 10% Montelukast or pharmaceutically acceptable salt thereof; wherein the total impurities resulting from the degradation of Montelukast in the composition are less than 1% after 6 months at 40° C. and 75% humidity. In some embodiments, a sulfoxide impurity in the stable topical formulation is less than 2% after 6 months at 40° C. and 75% humidity. In some embodiments, a cis-isomer impurity in the stable topical formulation is less than 1% after 6 months at 40° C. and 75% humidity. In some embodiments, a methylstyrene impurity in the stable topical formulation is less than 0.2% after 6 months at 40° C. and 75% humidity.

In some embodiments, the Montelukast is homogenously dispersed in the stable topical formulation for at least about 1 month. In some embodiments, the stable topical formulation is a gel. In some embodiments, the stable topical formulation is an emulsion. In some embodiments, the particle size of particles comprising Montelukast in the emulsion have a D90 of less than about 50 µm and greater than 5 µm, In some embodiments, the particle size of particles comprising Montelukast in the emulsion does not change greater than 20% over a period of three months at 25° C.

Methods of Treatment

The topical gel and topical emulsion described herein provide for stable formulations which are suitable for topical penetration of Montelukast into the skin. Thus, the present disclosure provides a formulation (e.g., emulsion or gel) suitable for topical administration for any condition in which Montelukast is effective for treatment, e.g., atopic dermatitis (i.e., atopic eczema), infantile atopic eczema, flexural eczema, prurigo Besnier, allergic eczema, and neurodermatitis. In some embodiments, the present disclosure provides a method for treating atopic dermatitis comprising administering the topical emulsion described herein. In some embodiments, the present disclosure provides a method for treating any inflammatory skin disease such as atopic dermatitis comprising administering the topical gel or emulsion described herein. In some embodiments, the present disclosure provides a method for treating infantile atopic eczema, flexural eczema, prurigo Besnier, allergic eczema, rosacea, and neurodermatitis comprising administering the topical emulsion or the topical gel as described herein.

In some embodiments, the disclosure provides for methods and stable topical formulations suitable for the treatment of erythema. The term "erythema" as used herein can refer to the increased/abnormal redness of the skin. In some embodiments, erythema refers to redness patches or localized areas. In some embodiments, the erythema is caused by an inflammatory response. In some embodiments, the erythema is not caused by an inflammatory response, e.g., is caused by an infection (e.g., cellulitis), a cancer, trauma to the skin (e.g., a wound), stress, insect bites, strep throat, fungal diseases, Behcet's disease, pregnancy, inflammatory bowel disease (e.g., Crohn's disease), or is a side effect caused by administration of a drug. In some embodiments, the formulations and methods described herein can be used to reduce erythema by at least one grade, as provided in Table A.

TABLE A

| Grade | Indication |
|---|---|
| None | No erythema |
| Mild | Faintly detectable erythema, very light pinkness |
| Moderate | Dull red, clearly distinguishable |
| Severe | Deep, dark red |

In some embodiments, the disclosure provides formulations and methods suitable to decrease erythema by 10% to 100%, 20% to 100%, 30% to 100%, 40% to 100%, 50% to 100%, 60% to 100%, 70% to 100% or 80% to 100% 7 days, 14 days, 21 days, or 28 days after administration of the formulations described herein. Methods of determining a reduction in erythema are known to the skilled artisan, e.g., in some embodiments the erythema percent change from placebo or from baseline can be determined by visual inspection, e.g., by a trained medical professional, e.g., by the doctor.

In some embodiments, the disclosure provides a method of reducing erythema in a subject suffering from atopic dermatitis, the method comprising topically administering to the subject a Montelukast formulation comprising at least 1% (wt/wt) Montelukast or pharmaceutically acceptable salt thereof for at least 10 days, e.g., at least 14 days, wherein the erythema is reduced by at least 5% from placebo. In some embodiments, the Montelukast formulation is a topical emulsion or a topical gel as described herein.

In some embodiments, the disclosure provides for stable topical formulation and methods suitable for the treatment of pruritus. The term "pruritus" as used herein can refer to uncomfortable, irritating sensation that makes you want to scratch your skin. In some embodiments, the pruritus is caused by an inflammatory response. In some embodiments, the pruritus is not caused by an inflammatory response, e.g., is caused by an infection (e.g., cellulitis), a cancer, trauma to the skin (e.g., a wound), stress, dry skin, insect bites, or is a side effect caused by administration of a drug. In some embodiments, the formulations and methods described herein can be used to reduce pruritus by at least one grade, as provided in Table B.

TABLE B

| Grade | Indication |
|---|---|
| None | No itching |
| Mild | Occasional, slight itching, not really bothersome |
| Moderate | Constant or intermittent itching that is somewhat bothersome |
| Severe | Intense itching that causes pronounced discomfort, disturbing normal activity |

In some embodiments, the disclosure provides formulations and methods suitable to decrease pruritus by 10% to 100%, 20% to 100%, 30% to 100%, 40% to 100%, 50% to 100%, 60% to 100%, 70% to 100% or 80% to 100% 7 days, 14 days, 21 days, or 28 days after administration of the formulations described herein. Methods of determining a reduction in pruritus are known to the skilled artisan, e.g., in some embodiments the pruritus percent change from placebo can be determined by visual inspection, e.g., by a trained medical professional, e.g., by the doctor.

In some embodiments, the disclosure provides a method of reducing pruritus in a subject suffering from atopic dermatitis, the method comprising topically administering to the subject a Montelukast formulation comprising at least 1% (wt/wt) Montelukast or pharmaceutically acceptable salt thereof for at least 10 days, e.g., at least 14 days, wherein the pruritus is reduced by at least 5% from placebo. In some embodiments, the Montelukast formulation is a topical emulsion or a topical gel as described herein.

In some embodiments, the disclosure provides for topical formulations and methods suitable for the treatment of induration. The term "induration" as used herein can refer to the increase in fibrous elements in skin tissue, thereby increasing the hardness of the skin. In some embodiments, the induration is caused by an inflammatory response. In some embodiments, the induration is not caused by an inflammatory response, e.g., is caused by an infection (e.g., cellulitis), a cancer, trauma to the skin (e.g., a wound), stress, insect bites, or is a side effect caused by administration of a drug. In some embodiments, the formulations and methods described herein can be used to reduce induration by at least one grade, as provided in Table C.

TABLE C

| Grade | Indication |
|---|---|
| None | No papulation/induration |
| Mild | Barely perceptible elevation |
| Moderate | Clearly perceptible elevation but not extensive |
| Severe | Marked and extensive elevation |

In some embodiments, the disclosure provides formulations and methods suitable to decrease induration by 10% to 100%, 20% to 100%, 30% to 100%, 40% to 100%, 50% to 100%, 60% to 100%, 70% to 100% or 80% to 100% 7 days, 14 days, 21 days, or 28 days after administration of the formulations described herein. Methods of determining a decrease in induration are known to the skilled artisan, e.g., in some embodiments the induration percent change from placebo can be determined by visual inspection, e.g., by a trained medical professional, e.g., by the doctor.

In some embodiments, the disclosure provides a method of reducing induration in a subject suffering from atopic dermatitis, the method comprising topically administering to the subject a Montelukast formulation comprising at least 1% (wt/wt) Montelukast or pharmaceutically acceptable salt thereof for at least 10 days, e.g., at least 14 days, wherein the induration is reduced by at least 5% from placebo. In some embodiments, the Montelukast formulation is a topical emulsion or a topical gel as described herein.

In some embodiments, the disclosure provides a topical formulation and methods suitable for the treatment of lichenification. The term "lichenification" refers to the thickening of the skin, or wherein the skin becomes leathery. In some embodiments, the lichenification includes increased markings, e.g., more pronounced wrinkles or creases in the skin. In some embodiments, lichenification includes hyperpigmentation. In some embodiments, the induration is caused by an inflammatory response. In some embodiments, the induration is not caused by an inflammatory response, e.g., is caused by constant scratching/rubbing of the skin (e.g., a repeated motion or as a result of an obsessive-compulsive disorder), an infection (e.g., cellulitis), a cancer, trauma to the skin (e.g., a wound), stress, insect bites, or is a side effect caused by administration of a drug. In some embodiments, the formulations and methods described herein can be used to reduce lichenification by at least one grade, as provided in Table D.

TABLE D

| Grade | Indication |
|---|---|
| None | No lichenification |
| Mild | Slight thickening of the skin discernible only by touch and with skin marking minimally exaggerated |
| Moderate | Definite thickening of the skin with skin marking exaggerated so that they form a visible criss-cross pattern |
| Severe | Thickened indurated skin with skin markings visibly portraying an exaggerated criss-cross pattern |

In some embodiments, the disclosure provides formulations and methods suitable to decrease lichenification by 10% to 100%, 20% to 100%, 30% to 100%, 40% to 100%, 50% to 100%, 60% to 100%, 70% to 100% or 80% to 100% 7 days, 14 days, 21 days, or 28 days after administration of the formulations described herein. Methods of determining a decrease in lichenification are known to the skilled artisan, e.g., in some embodiments the lichenification percent change from placebo can be determined by visual inspection, e.g., by a trained medical professional, e.g., by the doctor.

In some embodiments, the disclosure provides a method of reducing lichenification in a subject suffering from atopic dermatitis, the method comprising topically administering to the subject a Montelukast formulation comprising at least 1% (wt/wt) Montelukast or pharmaceutically acceptable salt thereof for at least 10 days, e.g., at least 14 days, wherein the lichenification is reduced by at least 5% from placebo. In some embodiments, the Montelukast formulation is a topical emulsion or a topical gel as described herein.

In some embodiments, the disclosure provides topical formulations and methods suitable for the reducing the Investigator Global Assessment (IGA) score in a subject. The IGA refers to the method as described in Eichenfield L F, et al., *J Am Acad Dermatol.* 2002; 46(4):495-504. In some embodiments, the formulations and methods described herein can be used to reduce the IGA score by at least one grade, as provided in Table E.

TABLE E

| Grade | Indication |
|---|---|
| Clear | No inflammatory signs |
| Almost Clear | Just perceptible erythema, and just perceptible papulation/infiltration |
| Mild | Mild erythema, and mild papulation/infiltration |
| Moderate | Moderate erythema, and moderate papulation/infiltration |
| Severe Disease | Severe erythema, and severe papulation/infiltration |
| Very Severe Disease | Severe erythema, and severe papulation/infiltration with oozing/crusting |

In some embodiments, the disclosure provides formulations and methods suitable to decrease the IGA score by 10% to 100%, 20% to 100%, 30% to 100%, 40% to 100%, 50% to 100%, 60% to 100%, 70% to 100% or 80% to 100% 7 days, 14 days, 21 days, or 28 days after administration of the formulations described herein. Methods of determining a decrease in IGA are known to the skilled artisan, e.g., in some embodiments the IGA percent change from placebo can be determined by visual inspection, e.g., by a trained medical professional, e.g., by the doctor.

In some embodiments, the disclosure provides a method of reducing the IGA score in a subject suffering from atopic dermatitis, the method comprising topically administering to the subject a Montelukast formulation comprising at least 1% (wt/wt) Montelukast or pharmaceutically acceptable salt thereof for at least 10 days, e.g., at least 14 days, wherein the IGA score is reduced by at least 5% from placebo. In some embodiments, the Montelukast formulation is a topical emulsion or a topical gel as described herein.

In some embodiments, the disclosure provides a topical formulation and methods suitable for the reduction of the Body Surface Area (BSA) affected score by the skin conditions described herein, e.g., atopic dermatitis. In some embodiments, the BSA score is reduced in a skin condition associated with an inflammatory response. In some embodiments, the BSA score is reduced in a skin condition not caused by an inflammatory response.

In some embodiments, the disclosure provides formulations and methods suitable to decrease the BSA score by 10% to 100%, 20% to 100%, 30% to 100%, 40% to 100%, 50% to 100%, 60% to 100%, 70% to 100% or 80% to 100%

7 days, 14 days, 21 days, or 28 days after administration of the formulations described herein.

In some embodiments, the disclosure provides a method of reducing the % BSA affected score in a subject suffering from atopic dermatitis, the method comprising topically administering to the subject a Montelukast formulation comprising at least 1% (wt/wt) Montelukast or pharmaceutically acceptable salt thereof for at least 10 days, e.g., at least 14 days, wherein the BSA score is reduced by at least 5% from placebo. In some embodiments, the Montelukast formulation is a topical emulsion or a topical gel as described herein.

In some embodiments, the disclosure provides method of treating atopic dermatitis (AD) in a population of subjects, the method comprising administering a topical pharmaceutical composition comprising 6.5% of Montelukast to a subject in the population of subjects, wherein the administration of the composition results in an improvement in one or more of the following parameters:

i. a decrease from baseline in mean Investigator's Global Assessment (IGA) score of at least 20% after 4 weeks. In some embodiments, the decrease from baseline in mean IGA score is at least 10%, at least 15%, at least 20%, at least 25%, at least 30%, at least 35%, at least 40%, at least 45% or at least 50% at 4 weeks. In some embodiments, the decrease from baseline in mean Investigator's Global Assessment (IGA) score is at least 20% at 2 weeks, 3 weeks, 4 weeks, 5 weeks, 6 weeks, 7 weeks, 8 weeks, 9 weeks or 10 weeks. In some embodiments, the decrease from baseline in mean IGA score is at least 10%, at least 15%, at least 20%, at least 25%, at least 30%, at least 35%, at least 40%, at least 45% or at least 50% at 2 weeks, 3 weeks, 4 weeks, 5 weeks, 6 weeks, 7 weeks, 8 weeks, 9 weeks or 10 weeks.

ii. a decrease from baseline in mean % Body Surface Area (BSA) affected score of at least 20% at 4 weeks. In some embodiments, the decrease from baseline in mean BSA is at least 10%, at least 15%, at least 20%, at least 25%, at least 30%, at least 35%, at least 40%, at least 45% or at least 50% at 4 weeks. In some embodiments, a decrease from baseline in mean % Body Surface Area (BSA) affected score of at least 20% at 2 weeks, 3 weeks, 4 weeks, 5 weeks, 6 weeks, 7 weeks, 8 weeks, 9 weeks or 10 weeks. In some embodiments, the decrease from baseline in mean BSA is at least 10%, at least 15%, at least 20%, at least 25%, at least 30%, at least 35%, at least 40%, at least 45% or at least 50% at 2 weeks, 3 weeks, 4 weeks, at 5 weeks, 6 weeks, 7 weeks, 8 weeks, 9 weeks or 10 weeks.

iii. a decrease from baseline in mean Erythema score of at least 20% at 4 weeks. In some embodiments, the decrease from baseline in mean Erythema score is at least 10%, at least 15%, at least 20%, at least 25%, at least 30%, at least 35%, at least 40%, at least 45% or at least 50% at 4 weeks. In some embodiments, a decrease from baseline in Erythema score of at least 20% at 2 weeks, 3 weeks, 4 weeks, 5 weeks, 6 weeks, 7 weeks, 8 weeks, 9 weeks or 10 weeks. In some embodiments, the decrease from baseline in mean Erythema score is at least 10%, at least 15%, at least 20%, at least 25%, at least 30%, at least 35%, at least 40%, at least 45% or at least 50% at 2 weeks, 3 weeks, 4 weeks, 5 weeks, 6 weeks, 7 weeks, 8 weeks, 9 weeks or 10 weeks.

iv. a decrease from baseline in mean Induration score of at least 15% at 4 weeks. In some embodiments, the decrease from baseline in mean Induration score is at least 5%, at least 10%, at least 15%, at least 20%, at least 25%, at least 30%, at least 35%, at least 40%, at least 45% or at least 50% at 4 weeks. In some embodiments, a decrease from baseline in mean Induration score of at least 15% at 2 weeks, 3 weeks, 4 weeks, 5 weeks, 6 weeks, 7 weeks, 8 weeks, 9 weeks or 10 weeks. In some embodiments, the decrease from baseline in mean Induration score is at least 5%, at least 10%, at least 15%, at least 20%, at least 25%, at least 30%, at least 35%, at least 40%, at least 45% or at least 50% at 2 weeks, 3 weeks, 4 weeks, 5 weeks, 6 weeks, 7 weeks, 8 weeks, 9 weeks or 10 weeks.

v. a decrease from baseline in mean Lichenification score of at least 25% at 4 weeks. In some embodiments, the decrease from baseline in mean Lichenification score is at least 10%, at least 15%, at least 20%, at least 25%, at least 30%, at least 35%, at least 40%, at least 45% or at least 50% at 4 weeks. In some embodiments, a decrease from baseline in mean Lichenification score of at least 25% at 2 weeks, 3 weeks, 4 weeks, 5 weeks, 6 weeks, 7 weeks, 8 weeks, 9 weeks or 10 weeks. In some embodiments, the decrease from baseline in mean Lichenification score is at least 10%, at least 15%, at least 20%, at least 25%, at least 30%, at least 35%, at least 40%, at least 45% or at least 50% at 2 weeks, 3 weeks, 4 weeks, 5 weeks, 6 weeks, 7 weeks, 8 weeks, 9 weeks or 10 weeks.

vi. a decrease from baseline in mean Pruritus score of at least 20% at 4 weeks. In some embodiments, the decrease from baseline in mean Pruritus score is at least 10%, at least 15%, at least 20%, at least 25%, at least 30%, at least 35%, at least 40%, at least 45% or at least 50% after 4 weeks. In some embodiments, a decrease from baseline in mean Pruritus score of at least 20% at 2 weeks, 3 weeks, 4 weeks, 5 weeks, 6 weeks, 7 weeks, 8 weeks, 9 weeks or 10 weeks. In some embodiments, the decrease from baseline in mean Pruritus score is at least 10%, at least 15%, at least 20%, at least 25%, at least 30%, at least 35%, at least 40%, at least 45% or at least 50% at 2 weeks, 3 weeks, 4 weeks, 5 weeks, 6 weeks, 7 weeks, 8 weeks, 9 weeks or 10 weeks.

In some embodiments, the atopic dermatitis described above is mild to moderate atopic dermatitis. In some embodiments, the 6.5% of Montelukast is administered twice daily to the subjects described above. In some embodiments, the 6.5% of Montelukast is administered for 1, 2, 3, 4, 5, 6, 7 or 8 weeks. In some embodiments, the 6.5% of montelukast is administered for 4 weeks to achieve the parameters listed above. In some embodiments, one of the parameters found in (i) to (vi) listed above is achieved. In some embodiments, 2, 3, 4, 5 or 6 of the parameters found in (i) to (vi) listed above are achieved.

In some embodiments, the disclosure provides a method of treating atopic dermatitis (AD) in a population of subjects, the method comprising administering a topical pharmaceutical composition comprising 6.5% of Montelukast to a subject in the population of subjects, wherein the administration of the composition results in an improvement in one or more of the following parameters:

(i) ≥20% difference between active and placebo in each respective treatment's % reduction from baseline for mean Investigator's Global Assessment (IGA) score after 4 weeks of treatment. In some embodiments, the method provides a ≥10%, ≥15%, ≥25%, ≥30%, ≥35%, ≥40%, ≥45% or ≥50% difference between active and placebo in % reduction from baseline for mean IGA score after 4 weeks of treatment. In some embodiments, the method provides a ≥10%, ≥15%, ≥25%, ≥30%, ≥35%, ≥40%, ≥45% or ≥50% difference between active and placebo in % reduction from baseline for mean IGA score at 2 weeks, 3 weeks, 4 weeks, 5 weeks, 6 weeks, 7 weeks, 8 weeks, 9 weeks or 10 weeks.

(ii) ≥20% difference between active and placebo in each respective treatment's % reduction from baseline for mean % Body Surface Area (BSA) affected score after 4 weeks of treatment. In some embodiments, the method provides a ≥10%, ≥15%, ≥25%, ≥30%, ≥35%, ≥40%, ≥45% or ≥50% difference between active and placebo in % reduction from baseline for mean % BSA affected score after 4 weeks of treatment. In some embodiments, the method provides a ≥10%, ≥15%, ≥25%, ≥30%, ≥35%, ≥40%, ≥45% or ≥50% difference between active and placebo in % reduction from baseline for mean % BSA affected score at 2 weeks, 3 weeks, 4 weeks, 5 weeks, 6 weeks, 7 weeks, 8 weeks, 9 weeks or 10 weeks.

(iii) ≥20% difference between active and placebo in each respective treatment's % reduction from baseline for mean Erythema score after 4 weeks of treatment. In some embodiments, the method provides a ≥10%, ≥15%, ≥25%, ≥30%, ≥35%, ≥40%, ≥45% or ≥50% difference between active and placebo in % reduction from baseline for mean Erythema score after 4 weeks of treatment. In some embodiments, the method provides a ≥10%, ≥15%, ≥25%, ≥30%, ≥35%, ≥40%, ≥45% or ≥50% difference between active and placebo in % reduction from baseline for mean Erythema score at 2 weeks, 3 weeks, 4 weeks, 5 weeks, 6 weeks, 7 weeks, 8 weeks, 9 weeks or 10 weeks.

(iv) ≥15% difference between active and placebo in each respective treatment's % reduction from baseline for mean Induration score after 4 weeks of treatment. In some embodiments, the method provides a ≥10%, ≥20%, ≥25%, ≥30%, ≥35%, ≥40%, ≥45% or ≥50% difference between active and placebo in % reduction from baseline for mean Induration score after 4 weeks of treatment. In some embodiments, the method provides a ≥10%, ≥20%, ≥25%, ≥30%, ≥35%, ≥40%, ≥45% or ≥50% difference between active and placebo in % reduction from baseline for mean Induration score at 2 weeks, 3 weeks, 4 weeks, 5 weeks, 6 weeks, 7 weeks, 8 weeks, 9 weeks or 10 weeks.

(v) ≥25% difference between active and placebo in each respective treatment's % reduction from baseline for mean Lichenification score after 4 weeks of treatment. In some embodiments, the method provides a ≥10%, ≥15%, ≥20%, ≥30%, ≥35%, ≥40%, ≥45% or ≥50% difference between active and placebo in % reduction from baseline for mean Lichenification score after 4 weeks of treatment. In some embodiments, the method provides a ≥10%, ≥15%, ≥20%, ≥30%, ≥35%, ≥40%, ≥45% or ≥50% difference between active and placebo in % reduction from baseline for mean Lichenification score at 2 weeks, 3 weeks, 4 weeks, 5 weeks, 6 weeks, 7 weeks, 8 weeks, 9 weeks or 10 weeks.

(vi) ≥20% difference between active and placebo in each respective treatment's % reduction from baseline for mean Pruritus score after 4 weeks of treatment. In some embodiments, the method provides a ≥10%, ≥15%, ≥25%, ≥30%, ≥35%, ≥40%, ≥45% or ≥50% difference between active and placebo in % reduction from baseline for mean Pruritus score after 4 weeks of treatment. In some embodiments, the method provides a ≥10%, ≥15%, ≥25%, ≥30%, ≥35%, ≥40%, ≥45% or ≥50% difference between active and placebo in % reduction from baseline for mean Pruritus score at 2 weeks, 3 weeks, 4 weeks, 5 weeks, 6 weeks, 7 weeks, 8 weeks, 9 weeks or 10 weeks.

In some embodiments, the atopic dermatitis described above is mild to moderate atopic dermatitis. In some embodiments, the 6.5% of Montelukast is administered twice daily to the subjects described above. In some embodiments, the 6.5% of Montelukast is administered for 1, 2, 3, 4, 5, 6, 7 or 8 weeks. In some embodiments, the 6.5% of Montelukast is administered for 4 weeks to achieve the parameters listed above. In some embodiments, one of the parameters found in (i) to (vi) listed above is achieved. In some embodiments, 2, 3, 4, 5 or 6 of the parameters found in (i) to (vi) listed above are achieved.

In some embodiments, the disclosure provides a method of treating atopic dermatitis (AD) in a population of subjects, the method comprising administering a topical pharmaceutical composition comprising 6.5% of Montelukast to the population of subjects, wherein the administration of the composition to the subjects results in an improvement in one or more of the following parameters:

(i) the percentage reduction in mean IGA score from baseline in the population of subjects administered the topical composition (i.e., the active group) following 4-week treatment is at least 5% higher than percentage reduction in mean IGA score from baseline in the placebo group (i.e., the subjects not administered the topical composition comprising montelukast). In some embodiments, the percentage reduction in mean IGA score from baseline in the active group following 4-week treatment is at least 10%, at least 15%, at least 20%, at least 25%, at least 30%, at least 35%, at least 40%, at least 45% or at least 50% higher than percentage reduction in mean IGA score from baseline in the placebo group. In some embodiments, the percentage reduction in mean IGA score from baseline in the active group following 2 weeks, 3 weeks, 4 weeks, 5 weeks, 6 weeks, 7 weeks, 8 weeks, 9 weeks or 10 weeks treatment is at least 5% higher than percentage reduction in mean IGA score from baseline in the placebo group. In some embodiments, the percentage reduction in mean IGA score from baseline in the active group following 2 weeks, 3 weeks, 4 weeks, 5 weeks, 6 weeks, 7 weeks, 8 weeks, 9 weeks or 10 weeks treatment is at least 10%, at least 15%, at least 20%, at least 25%, at least 30%, at least 35%, at least 40%, at least 45% or at least 50% higher than percentage reduction in mean IGA score from baseline in the placebo group;

(ii) the percentage reduction from baseline in mean % BSA affected score in the active group following 4-week treatment is at least 5% higher than mean % BSA affected score in the placebo group. In some embodiments, the percentage reduction from baseline in mean % BSA affected score in the active group following 4-week treatment is at least 10%, at least 15%, at least 20%, at least 25%, at least 30%, at least 35%, at least 40%, at least 45% or at least 50% higher than mean % BSA affected score in the placebo group. In some embodiments, the percentage reduction from baseline in mean % BSA affected score in the active group following 2 weeks, 3 weeks, 4 weeks, 5 weeks, 6 weeks, 7 weeks, 8 weeks, 9 weeks or 10 weeks treatment is at least 5% higher than mean % BSA affected score in the placebo group. In some embodiments, the percentage reduction from baseline in mean % BSA affected score in the active group following 2 weeks, 3 weeks, 4 weeks, 5 weeks, 6 weeks, 7 weeks, 8 weeks, 9 weeks or 10 weeks treatment is at least 10%, at least 15%, at least 20%, at least 25%, at least 30%, at least 35%, at least 40%, at least 45% or at least 50% higher than mean % BSA affected score in the placebo group;

(iii) the percentage reduction in mean Erythema score from baseline in the active group following 4-week treatment is at least 5% higher than mean Erythema score in the placebo group. In some embodiments, the percentage reduction in mean Erythema score from baseline in the active group following 4-week treatment is at least 10%, at least 15%, at least 20%, at least 25%, at least 30%, at least 35%, at least 40%, at least 45% or at least 50% higher than mean Erythema score in the placebo group. In some embodiments, the percentage reduction in mean Erythema score from baseline in the active group following 2 weeks, 3 weeks, 4 weeks, 5 weeks, 6 weeks, 7 weeks, 8 weeks, 9 weeks or 10 weeks treatment is at least 5% higher than mean Erythema score in the placebo group. In some embodiments, the percentage reduction in mean Erythema score from baseline in the active group following 2 weeks, 3 weeks, 4 weeks, 5 weeks, 6 weeks, 7 weeks, 8 weeks, 9 weeks or 10 weeks treatment is at least 10%, at least 15%, at least 20%, at least 25%, at least 30%, at least 35%, at least 40%, at least 45% or at least 50% higher than mean Erythema score in the placebo group;

(iv) the percentage reduction in mean Induration score from baseline in the active group following 4-week treatment is at least 5% higher than mean Induration score in the placebo group. In some embodiments, the percentage reduction in mean Induration score from baseline in the active group following 4-week treatment is at least 10%, at least 15%, at least 20%, at least 25%, at least 30%, at least 35%, at least 40%, at least 45% or at least 50% higher than mean Induration score in the placebo group. In some embodiments, the percentage reduction in mean Induration score from baseline in the active group following 2 weeks, 3 weeks, 4 weeks, 5 weeks, 6 weeks, 7 weeks, 8 weeks, 9 weeks or 10 weeks treatment is at least 5% higher than mean Induration score in the placebo group. In some embodiments, the percentage reduction in mean Induration score from baseline in the active group following 2 weeks, 3 weeks, 4 weeks, 5 weeks, 6 weeks, 7 weeks, 8 weeks, 9 weeks or 10 weeks treatment is at least 10%, at least 15%, at least 20%, at least 25%, at least 30%, at least 35%, at least 40%, at least 45% or at least 50% higher than mean Induration score in the placebo group;

(v) the percentage reduction in mean Lichenification score from baseline in the active group following 4-week treatment is at least 5% higher than mean Lichenification score in the placebo group. In some embodiments, the percentage reduction in mean Lichenification score from baseline in the active group following 4-week treatment is at least 10%, at least 15%, at least 20%, at least 25%, at least 30%, at least 35%, at least 40%, at least 45% or at least 50% higher than Lichenification score in the placebo group. In some embodiments, the percentage reduction in mean Lichenification score from baseline in the active group following 2 weeks, 3 weeks, 4 weeks, 5 weeks, 6 weeks, 7 weeks, 8 weeks, 9 weeks or 10 weeks treatment is at least 5% higher than mean Lichenification score in the placebo group. In some embodiments, the percentage reduction in mean Lichenification score from baseline in the active group following 2 weeks, 3 weeks, 4 weeks, 5 weeks, 6 weeks, 7 weeks, 8 weeks, 9 weeks or 10 weeks treatment is at least 10%, at least 15%, at least 20%, at least 25%, at least 30%, at least 35%, at least 40%, at least 45% or at least 50% higher than mean Lichenification score in the placebo group; and (vi) the percentage reduction in mean Pruritus score from baseline in the active group following 4-week treatment is at least 5% higher than mean Pruritus score in the placebo group. In some embodiments, the percentage reduction in mean Pruritus score from baseline in the active group following 4-week treatment is at least 10%, at least 15%, at least 20%, at least 25%, at least 30%, at least 35%, at least 40%, at least 45% or at least 50% higher than mean Pruritus score in the placebo group. In some embodiments, the percentage reduction in mean Pruritus score from baseline in the active group following 2 weeks, 3 weeks, 4 weeks, 5 weeks, 6 weeks, 7 weeks, 8 weeks, 9 weeks or 10 weeks treatment is at least 5% higher than mean Pruritus score in the placebo group. In some embodiments, the percentage reduction in mean Pruritus score from baseline in the active group following 2 weeks, 3 weeks, 4 weeks, 5 weeks, 6 weeks, 7 weeks, 8 weeks, 9 weeks or 10 weeks treatment is at least 10%, at least 15%, at least 20%, at least 25%, at least 30%, at least 35%, at least 40%, at least 45% or at least 50% higher than mean Pruritus score in the placebo group.

In some embodiments, the atopic dermatitis described above is mild to moderate atopic dermatitis. In some embodiments, the 6.5% of Montelukast is administered twice daily to the subjects described above. In some embodiments, the 6.5% of Montelukast is administered for 1, 2, 3, 4, 5, 6, 7 or 8 weeks. In some embodiments, the 6.5% of Montelukast is administered for 4 weeks to achieve the parameters listed above. In some embodiments, one of the parameters found in (i) to (vi) listed above is achieved. In some embodiments, 2, 3, 4, 5 or 6 of the parameters found in (i) to (vi) listed above are achieved In some embodiments, the disclosure provides a method of treating atopic dermatitis (AD) in a population of subjects, the method comprising administering a topical pharmaceutical composition comprising 6.5% of Montelukast to a subject in the population of subjects, wherein the administration of the composition results in an improvement in one or more of the following parameters:

(i) at least a 75% reduction from baseline mean IGA score after 4 weeks of treatment. In some embodiments, the disclosure provides a method of treating AD in a subject, the method comprising administering a topical pharmaceutical composition comprising 6.5% of Montelukast to the subject, wherein the subject has at least a 60%, 65%, 70%, 80%, 85%, 90%, 95% or 99% reduction from baseline mean IGA score at 4 weeks of treatment. In some embodiments, administration results in at least a 75% reduction from baseline mean IGA score after 2 weeks, 3 weeks, 4 weeks, 5 weeks, 6 weeks, 7 weeks, 8 weeks, 9 weeks, or 10 weeks of treatment. In some embodiments, the disclosure provides a method of treating AD in a subject, the method comprising administering a topical pharmaceutical composition comprising 6.5% of Montelukast to the subject, wherein the subject has at least a 60%, 65%, 70%, 80%, 85%, 90%, 95% or 99% reduction from baseline mean IGA score after 2 weeks, 3 weeks, 4 weeks, 5 weeks, 6 weeks, 7 weeks, 8 weeks, 9 weeks, or 10 weeks of treatment;
(ii) at least an 85% reduction from baseline mean % BSA affected score after 4 weeks of treatment. In some embodiments, the disclosure provides a method of treating AD in a subject, the method comprising administering a topical pharmaceutical composition comprising 6.5% of Montelukast to the subject, wherein the subject has at least a 60%, 65%, 70%, 75%, 80%, 90%, 95% or 99% reduction from baseline mean % BSA affected score at 4 weeks of treatment. In some embodiments, administration results in at least an 85% reduction from baseline mean % BSA affected score at 2 weeks, 3 weeks, 4 weeks, 5 weeks, 6 weeks, 7 weeks, 8 weeks, 9 weeks, or 10 weeks of treatment. In some embodiments, the disclosure provides a method of treating AD in a subject, the method comprising administering a topical pharmaceutical composition comprising 6.5% of Montelukast to the subject, wherein the subject has at least a 60%, 65%, 70%, 75%, 80%, 90%, 95% or 99% reduction from baseline mean % BSA affected score at 2 weeks, 3 weeks, 4 weeks, 5 weeks, 6 weeks, 7 weeks, 8 weeks, 9 weeks, or 10 weeks of treatment;
(iii) at least a 90% reduction from baseline mean Erythema score at 4 weeks of treatment. In some embodiments, the disclosure provides a method of treating AD in a subject, the method comprising administering a topical pharmaceutical composition comprising 6.5% of Montelukast to the subject, wherein the subject has at least a 60%, 65%, 70%, 75%, 80%, 85%, 95% or 99% reduction from baseline mean Erythema score at 4 weeks of treatment. In some embodiments, administration results in at least a 90% reduction from baseline mean Erythema score at 2 weeks, 3 weeks, 4 weeks, 5 weeks, 6 weeks, 7 weeks, 8 weeks, 9 weeks, or 10 weeks of treatment. In some embodiments, the disclosure provides a method of treating AD in a subject, the method comprising administering a topical pharmaceutical composition comprising 6.5% of Montelukast to the subject, wherein the subject has at least a 60%, 65%, 70%, 75%, 80%, 85%, 95% or 99% reduction from baseline mean Erythema score at 2 weeks, 3 weeks, 4 weeks, 5 weeks, 6 weeks, 7 weeks, 8 weeks, 9 weeks, or 10 weeks of treatment;
(iv) at least a 90% reduction from baseline mean Induration score at 4 weeks of treatment. In some embodiments, the disclosure provides a method of treating AD in a subject, the method comprising administering a topical pharmaceutical composition comprising 6.5% of Montelukast to the subject, wherein the subject has at least a 60%, 65%, 70%, 75%, 80%, 85%, 93%, 95%, 97% or 99% reduction from baseline mean Induration score at 4 weeks of treatment. In some embodiments, administration results in at least a 90% reduction from baseline mean Induration score at 2 weeks, 3 weeks, 4 weeks, 5 weeks, 6 weeks, 7 weeks, 8 weeks, 9 weeks, or 10 weeks of treatment. In some embodiments, the disclosure provides a method of treating AD in a subject, the method comprising administering a topical pharmaceutical composition comprising 6.5% of Montelukast to the subject, wherein the subject has at least a 60%, 65%, 70%, 75%, 80%, 85%, 93%, 95%, 97% or 99% reduction from baseline mean Induration score at 2 weeks, 3 weeks, 4 weeks, 5 weeks, 6 weeks, 7 weeks, 8 weeks, 9 weeks, or 10 weeks of treatment;
(v) at least a 90% reduction from baseline mean Lichenification score at 4 weeks of treatment. In some embodiments, the disclosure provides a method of treating AD in a subject, the method comprising administering a topical pharmaceutical composition comprising 6.5% of Montelukast to the subject, wherein the subject has at least a 60%, 65%, 70%, 75%, 80%, 85%, 93%, 95%, 97% or 99% reduction from baseline mean Lichenification score at 4 weeks of treatment. In some embodiments, administration results in at least a 90% reduction from baseline mean Lichenification score at 2 weeks, 3 weeks, 4 weeks, 5 weeks, 6 weeks, 7 weeks, 8 weeks, 9 weeks, or 10 weeks of treatment. In some embodiments, the disclosure provides a method of treating AD in a subject, the method comprising administering a topical pharmaceutical composition comprising 6.5% of Montelukast to the subject, wherein the subject has at least a 60%, 65%, 70%, 75%, 80%, 85%, 93%, 95%, 97% or 99% reduction from baseline mean Lichenification score at 2 weeks, 3 weeks, 4 weeks, 5 weeks, 6 weeks, 7 weeks, 8 weeks, 9 weeks, or 10 weeks of treatment; and
(vi) at least an 85% reduction from baseline mean Pruritus score at 4 weeks of treatment. In some embodiments, the disclosure provides a method of treating AD in a subject, the method comprising administering a topical pharmaceutical composition comprising 6.5% of Montelukast to the subject, wherein the subject has at least a 60%, 65%, 70%, 75%, 80%, 90%, 95% or 99% reduction from baseline mean Pruritus score at 4 weeks of treatment. In some embodiments, administration results in at least an 85% reduction from baseline mean Pruritus score at 2 weeks, 3 weeks, 4 weeks, 5 weeks, 6 weeks, 7 weeks, 8 weeks, 9 weeks, or 10 weeks of treatment. In some embodiments, the disclosure provides a method of treating AD in a subject, the method comprising administering a topical pharmaceutical composition comprising 6.5% of Montelukast to the subject, wherein the subject has at least a 60%, 65%, 70%, 75%, 80%, 90%, 95% or 99% reduction from baseline mean Pruritus score at 2 weeks, 3 weeks, 4 weeks, 5 weeks, 6 weeks, 7 weeks, 8 weeks, 9 weeks, or 10 weeks of treatment;

In some embodiments, the atopic dermatitis described above is mild to moderate atopic dermatitis. In some embodiments, the 6.5% of Montelukast is administered twice daily to the subjects described above. In some embodiments, the 6.5% of Montelukast is administered for 1, 2, 3, 4, 5, 6, 7 or 8 weeks. In some embodiments, the 6.5% of Montelukast is administered for 4 weeks to achieve the parameters listed above. In some embodiments, one of the parameters found in (i) to (vi) listed above is achieved. In some embodiments, 2, 3, 4, 5 or 6 of the parameters found in (i) to (vi) listed above are achieved.

In some embodiments, the disclosure provides a method of treating atopic dermatitis (AD) in a population of subjects, the method comprising administering to the population of subjects twice daily for 4 weeks a topical pharmaceutical composition comprising 6.5% of montelukast, wherein the administration of the composition to the population of subjects results in an improvement in one or more of the following parameters:
(i) the percentage of subjects with a 2- or more grade improvement from baseline in IGA score is at least 5% higher than placebo after the 4 weeks. In some embodiments, the percentage of subjects with a 2- or more grade improvement from baseline in IGA score is at least 10%, at least 15%, at least 20%, at least 25%, at least 30%, at least 35%, at least 40%, at least 45% or at least 50% higher than placebo after the 4 weeks. In some embodiments, the percentage of subjects with a 1- or more grade improvement from baseline in IGA score is at least 5%, at least 10%, at least 15%, at least 20%, at least 25%, at least 30%, at least 35%, at least 40%, at least 45% or at least 50% higher than placebo after the 4 weeks. In some embodiments, the percentage of subjects with a 2- or more grade improvement from baseline in IGA score is at least 5% higher than placebo at 2 weeks, 3 weeks, 4 weeks, 5 weeks, 6 weeks, 7 weeks, 8 weeks, 9 weeks, or 10 weeks of treatment. In some embodiments, the percentage of subjects with a 2- or more grade improvement from baseline in IGA score is at least 10%, at least 15%, at least 20%, at least 25%, at least 30%, at least 35%, at least 40%, at least 45% or at least 50% higher than placebo at 2 weeks, 3 weeks, 4 weeks, 5 weeks, 6 weeks, 7 weeks, 8 weeks, 9 weeks, or 10 weeks of treatment. In some embodiments, the percentage of subjects with a 1- or more grade improvement from baseline in IGA score is at least 5%, at least 10%, at least 15%, at least 20%, at least 25%, at least 30%, at least 35%, at least 40%, at least 45% or at least 50% higher than placebo at 2 weeks, 3 weeks, 4 weeks, 5 weeks, 6 weeks, 7 weeks, 8 weeks, 9 weeks, or 10 weeks of treatment;

(ii) the percentage of subjects with a 2 or more grade improvement from baseline in % BSA affected score is at least 5% higher than placebo after the 4 weeks. In some embodiments, the percentage of subjects with a 2- or more grade improvement from baseline is at least 10%, at least 15%, at least 20%, at least 25%, at least 30%, at least 35%, at least 40%, at least 45% or at least 50% higher than placebo in a % BSA affected after the 4 weeks. In some embodiments, the percentage of subjects with a 1- or more grade improvement from baseline is at least 5%, at least 10%, at least 15%, at least 20%, at least 25%, at least 30%, at least 35%, at least 40%, at least 45% or at least 50% higher than placebo % BSA affected score after the 4 weeks. In some embodiments, the percentage of subjects with a 2- or more grade improvement from baseline in % BSA affected score is at least 5% higher than placebo at 5 weeks, 6 weeks, 7 weeks, 8 weeks, 9 weeks, or 10 weeks of treatment. In some embodiments, the percentage of subjects with a 2- or more grade improvement from baseline is at least 10%, at least 15%, at least 20%, at least 25%, at least 30%, at least 35%, at least 40%, at least 45% or at least 50% higher than placebo in a % BSA affected score at 5 weeks, 6 weeks, 7 weeks, 8 weeks, 9 weeks, or 10 weeks of treatment. In some embodiments, the percentage of subjects with a 1- or more grade improvement from baseline is at least 5%, at least 10%, at least 15%, at least 20%, at least 25%, at least 30%, at least 35%, at least 40%, at least 45% or at least 50% higher than placebo % BSA affected score at 5 weeks, 6 weeks, 7 weeks, 8 weeks, 9 weeks, or 10 weeks of treatment;

(iii) the percentage of subjects with a 2- or more grade improvement from baseline in Erythema score is at least 5% higher than placebo after the 4 weeks. In some embodiments, the percentage of subjects with a 2- or more grade improvement from baseline in Erythema score is at least 10%, at least 15%, at least 20%, at least 25%, at least 30%, at least 35%, at least 40%, at least 45% or at least 50% higher than placebo after the 4 weeks. In some embodiments, the percentage of subjects with a 1- or more grade improvement from baseline in an Erythema score is at least 5%, at least 10%, at least 15%, at least 20%, at least 25%, at least 30%, at least 35%, at least 40%, at least 45% or at least 50% higher than placebo after the 4 weeks. In some embodiments, the percentage of subjects with a 2- or more grade improvement from baseline in Erythema score is at least 5% higher than placebo at 2 weeks, 3 weeks, 4 weeks, 5 weeks, 6 weeks, 7 weeks, 8 weeks, 9 weeks, or 10 weeks of treatment. In some embodiments, the percentage of subjects with a 2- or more grade improvement from baseline in Erythema score is at least 10%, at least 15%, at least 20%, at least 25%, at least 30%, at least 35%, at least 40%, at least 45% or at least 50% higher than placebo at 2 weeks, 3 weeks, 4 weeks, 5 weeks, 6 weeks, 7 weeks, 8 weeks, 9 weeks, or 10 weeks of treatment. In some embodiments, the percentage of subjects with a 1- or more grade improvement from baseline in an Erythema score is at least 5%, at least 10%, at least 15%, at least 20%, at least 25%, at least 30%, at least 35%, at least 40%, at least 45% or at least 50% higher than placebo at 2 weeks, 3 weeks, 4 weeks, 5 weeks, 6 weeks, 7 weeks, 8 weeks, 9 weeks, or 10 weeks of treatment;

(iv) the percentage of subjects with a 2- or more grade improvement from baseline in Induration score is at least 5% higher than placebo after the 4 weeks. In some embodiments, the percentage of subjects with a 2- or more grade improvement from baseline in an Induration score is at least 10%, at least 15%, at least 20%, at least 25%, at least 30%, at least 35%, at least 40%, at least 45% or at least 50% higher than placebo after the 4 weeks. In some embodiments, the percentage of subjects with a 1- or more grade improvement from baseline in Induration score is at least 5%, at least 10%, at least 15%, at least 20%, at least 25%, at least 30%, at least 35%, at least 40%, at least 45% or at least 50% higher than placebo after the 4 weeks. In some embodiments, the percentage of subjects with a 2- or more grade improvement from baseline in Induration score is at least 5% higher than placebo at 2 weeks, 3 weeks, 4 weeks, 5 weeks, 6 weeks, 7 weeks, 8 weeks, 9 weeks, or 10 weeks of treatment. In some embodiments, the percentage of subjects with a 2- or more grade improvement from baseline in an Induration score is at least 10%, at least 15%, at least 20%, at least 25%, at least 30%, at least 35%, at least 40%, at least 45% or at least 50% higher than placebo at 2 weeks, 3 weeks, 4 weeks, 5 weeks, 6 weeks, 7 weeks, 8 weeks, 9 weeks, or 10 weeks of treatment. In some embodiments, the percentage of subjects with a 1- or more grade improvement from baseline in Induration score is at least 5%, at least 10%, at least 15%, at least 20%, at least 25%, at least 30%, at least 35%, at least 40%, at least 45% or at least 50% higher than placebo at 2 weeks, 3 weeks, 4 weeks, 5 weeks, 6 weeks, 7 weeks, 8 weeks, 9 weeks, or 10 weeks of treatment;

(v) the percentage of subjects with a 2- or more grade improvement from baseline in Lichenification score is at least 5% higher than placebo after the 4 weeks. In some embodiments, the percentage of subjects with a 2- or more grade improvement from baseline in Lichenification score is at least 10%, at least 15%, at least 20%, at least 25%, at least 30%, at least 35%, at least 40%, at least 45% or at least 50% higher than placebo after the 4 weeks. In some embodiments, the percentage of subjects with a 1- or more grade improvement from baseline in Lichenification score is at least 5%, at least 10%, at least 15%, at least 20%, at least 25%, at least 30%, at least 35%, at least 40%, at least 45% or at least 50% higher than placebo after the 4 weeks. In some embodiments, the percentage of subjects with a 2- or more grade improvement at 2 weeks, 3 weeks, 4 weeks, 5 weeks, 6 weeks, 7 weeks, 8 weeks, 9 weeks, or 10 weeks of treatment. In some embodiments, the percentage of subjects with a 2- or more grade improvement from baseline in Lichenification score is at least 10%, at least 15%, at least 20%, at least 25%, at least 30%, at least 35%, at least 40%, at least 45% or at least 50% higher than placebo at 2 weeks, 3 weeks, 4 weeks, 5 weeks, 6 weeks, 7 weeks, 8 weeks, 9 weeks, or 10 weeks of treatment. In some embodiments, the percentage of subjects with a 1- or more grade improvement from baseline in Lichenification score is at least 5%, at least 10%, at least 15%, at least 20%, at least 25%, at least 30%, at least 35%, at least 40%, at least 45% or at least 50% higher than placebo at 2 weeks, 3 weeks, 4 weeks, 5 weeks, 6 weeks, 7 weeks, 8 weeks, 9 weeks, or 10 weeks of treatment; and (vi) the percentage of subjects with a 2- or more grade improvement from baseline in Pruritus score is at least 5% higher than placebo after the 4 weeks. In some embodiments, the percentage of subjects with a 2- or more grade improvement from baseline in Pruritus score is at least 10%, at least 15%, at least 20%, at least 25%, at least 30%, at least 35%, at least 40%, at least 45% or at least 50% higher than placebo after the 4 weeks. In some embodiments, the percentage of subjects with a 1- or more grade improvement from baseline in a Pruritus score is at least 5%, at least 10%, at least 15%, at least 20%, at least 25%, at least 30%, at least 35%, at least 40%, at least 45% or at least 50% higher than placebo after the 4 weeks. In some embodiments, the percentage of subjects with a 2- or more grade improvement from baseline in Pruritus score is at least 5% higher than placebo at 2 weeks, 3 weeks, 4 weeks, 5 weeks, 6 weeks, 7 weeks, 8 weeks, 9 weeks, or 10 weeks of treatment. In some embodiments, the percentage of subjects with a 2- or more grade improvement from baseline in Pruritus score is at least 10%, at least 15%, at least 20%, at least 25%, at least 30%, at least 35%, at least 40%, at least 45% or at least 50% higher than placebo at 2 weeks, 3 weeks, 4 weeks, 5 weeks, 6 weeks, 7 weeks, 8 weeks, 9 weeks, or 10 weeks of treatment. In some embodiments, the percentage of subjects with a 1- or more grade improvement from baseline in a Pruritus score is at least 5%, at least 10%, at least 15%, at least 20%, at least 25%, at least 30%, at least 35%, at least 40%, at least 45% or at least 50% higher than placebo at 2 weeks, 3 weeks, 4 weeks, 5 weeks, 6 weeks, 7 weeks, 8 weeks, 9 weeks, or 10 weeks of treatment.

In some embodiments, the atopic dermatitis described above is mild to moderate atopic dermatitis. In some embodiments, the 6.5% of Montelukast is administered twice daily to the subjects described above. In some embodiments, the 6.5% of Montelukast is administered for 1, 2, 3, 4, 5, 6, 7 or 8 weeks. In some embodiments, the 6.5% of Montelukast is administered for 4 weeks to achieve the parameters listed above. In some embodiments, one of the parameters found in (i) to (vi) listed above is achieved. In some embodiments, 2, 3, 4, 5 or 6 of the parameters found in (i) to (vi) listed above are achieved.

In some embodiments, the disclosure provides a method of treating atopic dermatitis (AD) in a subject, the method comprising administering a topical pharmaceutical composition comprising 6.5% of Montelukast to the subject, wherein the administration results in a reduction of Investigator's Static Global Assessment (ISGA) score, where the percentage of subjects with a 2- or more grade improvement from baseline in ISGA score is at least 5% higher than placebo after the 4 weeks. In some embodiments, the percentage of subjects with a 2- or more grade improvement from baseline in ISGA score is at least 10%, at least 15%, at least 20%, at least 25%, at least 30%, at least 35%, at least 40%, at least 45% or at least 50% higher than placebo after the 4 weeks. In some embodiments, the percentage of subjects with a 1- or more grade improvement from baseline in a ISGA score is at least 5%, at least 10%, at least 15%, at least 20%, at least 25%, at least 30%, at least 35%, at least 40%, at least 45% or at least 50% higher than placebo after the 4 weeks. In some embodiments, the percentage of subjects with a 2- or more grade improvement from baseline in ISGA score is at least 5% higher than placebo at 2 weeks, 3 weeks, 4 weeks, 5 weeks, 6 weeks, 7 weeks, 8 weeks, 9 weeks, or 10 weeks of treatment. In some embodiments, the percentage of subjects with a 2- or more grade improvement from baseline in ISGA score is at least 10%, at least 15%, at least 20%, at least 25%, at least 30%, at least 35%, at least 40%, at least 45% or at least 50% higher than placebo at 2 weeks, 3 weeks, 4 weeks, 5 weeks, 6 weeks, 7 weeks, 8 weeks, 9 weeks, or 10 weeks of treatment. In some embodiments, the percentage of subjects with a 1- or more grade improvement from baseline in a ISGA score is at least 5%, at least 10%, at least 15%, at least 20%, at least 25%, at least 30%, at least 35%, at least 40%, at least 45% or at least 50% higher than placebo at 2 weeks, 3 weeks, 4 weeks, 5 weeks, 6 weeks, 7 weeks, 8 weeks, 9 weeks, or 10 weeks of treatment.

In some embodiments, the disclosure provides a method of treating atopic dermatitis (AD) in a subject, the method comprising administering a topical pharmaceutical composition comprising 6.5% of Montelukast to the subject, wherein the administration results in at least >5% difference between active and placebo treatments in EASI-75. In some embodiments, the administration results in at least >6%, at least >7%, at least >8%, at least >9%, at least >10%, at least >12%, at least >15%, at least >18%, at least >20%, or at least >25%, difference between active and placebo treatments in EASI-75. In some embodiments, the administration results in at least >6%, at least >7%, at least >8%, at least >9%, at least >10%, at least >12%, at least >15%, at least >18%, at least >20%, or at least >25%, difference between active and placebo treatments in EASI-50. In some embodiments, the administration results in at least >6%, at least >7%, at least >8%, at least >9%, at least >10%, at least >12%, at least >15%, at least >18%, at least >20%, or at least >25%, difference between active and placebo treatments in EASI-90. In some embodiments, the administration results in at least >6%, at least >7%, at least >8%, at least >9%, at least >10%, at least >12%, at least >15%, at least >18%, at least >20%, or at least >25%, difference between active and placebo treatments in EASI-75 at 2 weeks, 3 weeks, 4 weeks, at 5 weeks, at 6 weeks, at 7 weeks, at 8 weeks, at 9 weeks or at 10 weeks.

In some embodiments, the disclosure provides a method of treating atopic dermatitis (AD) in a subject, the method comprising administering a topical pharmaceutical composition comprising 6.5% of Montelukast to the subject, wherein the administration results in a reduction of at least one symptom selected from erythema, pruritus, induration and lichenification compared to a placebo as measured by at least a 2-grade improvement from baseline by 2 weeks these symptoms. In some embodiments, the method comprises administering a topical pharmaceutical composition comprising 6.5% of Montelukast to the subject, wherein the administration results in a reduction of at least one symptom selected from erythema, pruritus, induration and lichenification compared to a placebo as measured by a 2-week success profile comprising at least a 1-grade improvement from baseline of the symptoms. In some embodiments, the method comprises administering a topical pharmaceutical composition comprising 6.5% of Montelukast to the subject, wherein the administration results in a reduction of at least one symptom selected from erythema, pruritus, induration and lichenification compared to a placebo as measured by a 2-week success profile comprising at least a 3-grade improvement from baseline of the symptoms.

In some embodiments, the disclosure provides a method for topically administering Montelukast for the treatment of atopic dermatitis (AD), without significant systemic exposure of the montelukast. Minimizing systemic exposure of Montelukast can decrease adverse side effects of Montelukast, including but not limited to body aches or pain, cough, difficulty in breathing, dryness or soreness of the throat, fever, headache, loss of voice, pain or tenderness around the eyes and cheekbones, pain, redness, or swelling in the ear, stomach pain, stuffy or runny nose, tender, swollen glands in neck, trouble in swallowing, unusual tiredness or weakness, voice changes, upper respiratory infection, diarrhea, earache or ear infection, flu, runny nose, neuropsychiatric side effect and sinus infection. Thus, in some embodiments, the disclosure provides a method of reducing side effect associated with Montelukast by topically administering a topical pharmaceutical composition comprising 6.5% of Montelukast to the subject. In some embodiments, the disclosure provides a method of treating atopic dermatitis (AD) in a subject, the method comprising topically administering twice daily to the subject a topical pharmaceutical composition comprising 6.5% of Montelukast, wherein the twice daily topical administration provides less than 50 ng/mL, less than 30 ng/mL, less than 20 ng/mL, less than 15 ng/mL, less than 10 ng/mL, less than 8 ng/mL, less than 6 ng/mL, less than 5 ng/mL, less than 4 ng/mL, less than 3 ng/mL, or less than 2 ng/mL Montelukast in the plasma of the subject after 14 days of administration. In some embodiments, the disclosure provides a method of treating atopic dermatitis (AD) in a subject, the method comprising topically administering twice daily to the subject a topical pharmaceutical composition comprising 6.5% of Montelukast, wherein the twice daily topical administration provides less than 3 ng/mL montelukast in the plasma of the subject after 14 days of administration.

In some embodiments, the disclosure provides a method of treating atopic dermatitis (AD) in a population of subjects, the method comprising topically administering twice daily to the population of subjects a topical pharmaceutical composition comprising 6.5% of Montelukast, wherein the twice daily topical administration provides (i.e., $C_{max}$) less than 200 ng/mL, less than 100 ng/mL, less than 50 ng/mL less than 30 ng/mL, less than 20 ng/mL, less than 15 ng/mL, less than 10 ng/mL, less than 8 ng/mL, less than 6 ng/mL, less than 5 ng/mL, less than 4 ng/mL, less than 3 ng/mL, or less than 2 ng/mL montelukast in the plasma in at least 60%, at least 70%, at least 75%, at least 80%, at least 85%, or at least 90% of the subjects in the population of subjects.

In some embodiments, the plasma level of Montelukast after topical administration is dependent on the amount of surface area on which the Montelukast composition is being administered. In some embodiments, the Montelukast is administered only to the affected area, the area affected with atopic dermatitis. In some embodiments, the Montelukast is administered to an area of about 1 cm' to about 100 cm$^2$, about 2 cm to about 80 cm$^2$, about 3 cm$^2$ to about 60 cm$^2$, about 4 cm$^2$ to about 40 cm$^2$. In some embodiments, the Montelukast is administered to an area which is between 1-30% of the total body surface area of the subject. In some embodiments, the Montelukast is administered to an area which is 5% and above of the total body surface area of the subject.

In some embodiments, administration is accomplished by applying a thin layer of the topical emulsion or topical gel to the affected skin area. The amount of the topical gel or the topical emulsion applied will vary according to several factors, including, but not limited to, the size of the affected area, the severity of the condition, and the concentration of Montelukast in the topical gel or topical emulsion.

In some embodiments, the topical gel or topical emulsion are applied one to six times each day, one to four times each day, one to three times each day, one to two times each day. In some embodiments, the topical gel or topical emulsion are applied as needed, or when symptoms appear. In some embodiments, the topical gel or topical emulsion can be applied daily for one day, greater than one day, greater than one week, or greater than one month. In some embodiments, the topical gel or topical emulsion are applied until after the symptoms of the condition being treated have been alleviated. In some embodiments, the topical gel or topical emulsion can be applied before the onset of symptoms. In some embodiments, the topical gel or topical emulsion can be applied every day, every two days, every three days, every four days, twice a week, once a week, etc., as can be determined by the skilled artisan for the treatment of a condition.

In some embodiments, the topical gel or topical emulsions as described herein can be used for treating atopic dermatitis in a human, e.g., a male or a female. In some embodiments, the topical gel or topical emulsions as described herein can be used for treating atopic dermatitis in a human infant (0 to 2 years old), a human child (2 to 12 years old), a human adolescent (12 to 18 years old) or a human adult (older than 18 years old). In some embodiments, the topical gel or topical emulsions as described herein can be used for treating atopic dermatitis in an animal, i.e., non-human, such as a domesticated animal such as a dog, cat, cow, horse, or a zoo animal.

The topical gel or topical emulsion as described herein can be administered topically. When administered by a topical route, the topical gel or topical emulsion is administered in a quantity that is sufficient to cover the affected area with the topical gel or topical emulsion. In some embodiments, the topical gel or topical emulsion is applied to the affected with a layer of approximately 0.01 mm to 5 mm thickness or about 0.5 mm to 2 mm thickness. The topical gel or topical emulsion may be in the form of a cream, gel, patch, foam, lotion, suspension, ointment, topical swab, emulsion, paste, shampoo, solution or spray. The topical gel or topical emulsion can be applied with or without applicator. For example, in some embodiments, the topical gel or topical emulsion is applied with an applicator, e.g., cloth, a swab, a wipe or a patch. In some embodiments, the topical gel or topical emulsion is pre-applied to the applicator, e.g., is a medicated cloth, a medicated swab, a medicated wipe or a medicated patch.

All references cited herein, including patents, patent applications, papers, textbooks and the like, and the references cited therein, to the extent that they are not already, are hereby incorporated herein by reference in their entirety.

EMBODIMENTS

Embodiment 1. A topical emulsion comprising
about 0.5% to about 10% Montelukast or pharmaceutically acceptable salt thereof;
and
about 0.4% to about 4% carbomer;
wherein the particles comprising the Montelukast in the emulsion have D90 of less than about 50 wherein the Montelukast or pharmaceutically acceptable salt thereof is homogeneously dispersed in the emulsion, and wherein the emulsion has a pH of about 3.0 to about 6.5.

Embodiment 2. The topical emulsion of embodiment 1, wherein the particles have D90 of less than about 40 μm.

Embodiment 3. The topical emulsion of embodiment 1, wherein the particles have D90 of less than about 20 μm.

Embodiment 4. The topical emulsion of any one of embodiments 1 to 3, wherein the particles have D90 of greater than about 8 μm.

Embodiment 5. The topical emulsion of any one of embodiments 1 to 3, wherein the particles have D90 of about 10 μm to about 20 μm.

Embodiment 6. The topical emulsion of any one of embodiments 1 to 5, wherein the particles have D50 of less than about 30 μm.

Embodiment 7. The topical emulsion of any one of embodiments 1 to 5, wherein the particles have D50 of less than about 25 μm.

Embodiment 8. The topical emulsion of any one of embodiments 1 to 5, wherein the particles have D50 of less than about 15 μm.

Embodiment 9. The topical emulsion of any one of embodiments 1 to 5, wherein the particles have D50 of less than about 5 μm.

Embodiment 10. The topical emulsion of any one of embodiments 1 to 9, wherein the particles have D10 of less than about 7 μm.

Embodiment 11. The topical emulsion of any one of embodiments 1 to 9, wherein the particles have D10 of greater than about 3 μm.

Embodiment 12. The topical emulsion of any one of embodiments 1 to 11, wherein the average particle size of the particles does not change greater than 10% over a period of 3 months at 25° C.

Embodiment 13. The topical emulsion of any one of embodiments 1 to 12, wherein the Montelukast in the emulsion is about 70% to 95% in the particles as Montelukast acid Form I, and about 5% to about 30% is not in the particles.

Embodiment 14. The topical emulsion of any one of embodiments 1 to 13, wherein the Montelukast in the particles is Montelukast acid Form I.

Embodiment 15. The topical emulsion of any one of embodiments 1 to 14, wherein the emulsion comprises about 4% to about 8% Montelukast.

Embodiment 16. The topical emulsion of any one of embodiments 1 to 15, wherein the emulsion comprises about 40% to about 70% water.

Embodiment 17. The topical emulsion of any one of embodiments 1 to 16, further comprising a penetration enhancer.

Embodiment 18. The topical emulsion of any one of embodiments 1 to 17, wherein the penetration enhancer is DMSO.

Embodiment 19. The topical emulsion of any one of embodiments 1 to 18, wherein the emulsion comprises less than 5% DMSO.

Embodiment 20. The topical emulsion of any one of embodiments 1 to 19, wherein the emulsion comprises less than 3% DMSO.

Embodiment 21. The topical emulsion of any one of embodiments 1 to 20, wherein the emulsion comprises less than 10% alcohol.

Embodiment 22. The topical emulsion of any one of embodiments 1 to 21, wherein the emulsion comprises less than 5% alcohol.

Embodiment 23. The topical emulsion of any one of embodiments 1 to 22, wherein the emulsion comprises less than 2% $C_1$-$C_5$ alcohol.

Embodiment 24. The topical emulsion of any one of embodiments 1 to 23, further comprising a preservative, an amphiphilic compound, an emulsifier, a lubricant, or combinations thereof.

Embodiment 25. The topical emulsion of embodiment 24, wherein the preservative is an antioxidant.

Embodiment 26. The topical emulsion of embodiment 25, wherein the antioxidant comprises BHT, BHA or combinations thereof.

Embodiment 27. The topical emulsion of embodiment 24, wherein the amphiphilic compound comprises oleyl alcohol, polyoxyglycerides, propylene carbonate, propylene glycol, or combinations thereof.

Embodiment 28. The topical emulsion of embodiment 27, wherein the amphiphilic compound is propylene glycol.

Embodiment 29. The topical emulsion of embodiment 24, wherein the emulsifier is a polysorbate.

Embodiment 30. The topical emulsion of embodiment 24, wherein the lubricant is polypropylene glycol stearyl ether.

Embodiment 31. The topical emulsion of any one of embodiments 1 to 30, wherein the total impurities in the emulsion are less than 2% after 12 months at 25° C.

Embodiment 32. The topical emulsion of any one of embodiments 1 to 30, wherein the total impurities in the emulsion are less than 0.5% after 12 months at 25° C.

Embodiment 33. The topical emulsion of any one of embodiments 1 to 32, wherein the sulfoxide impurity in the emulsion is less than 2% after 12 months at 25° C.

Embodiment 34. The topical emulsion of any one of embodiments 1 to 33, wherein the sulfoxide impurity in the emulsion is less than 0.5% after 12 months at 25° C.

Embodiment 35. The topical emulsion of any one of embodiments 1 to 34, wherein the cis-isomer impurity in the emulsion is less than 1% after 12 months at 25° C.

Embodiment 36. The topical emulsion of any one of embodiments 1 to 35, wherein the methylstyrene impurity in the emulsion is less than 0.2% after 12 months at 25° C.

Embodiment 37. The topical emulsion of any one of embodiments 1 to 36, wherein the emulsion has a maximum globule size of less than about 100 μm.

Embodiment 38. The topical emulsion of any one of embodiments 1 to 36, wherein the emulsion has a maximum globule size of less than about 20 μm.

Embodiment 39. A method of treating atopic dermatitis comprising administering the topical emulsion of embodiments 1 to 38.

Embodiment 40. A method of treating erythema comprising administering the topical emulsion of embodiments 1 to 38.

Embodiment 41. A method of treating pruritus comprising administering the topical emulsion of embodiments 1 to 38.

Embodiment 42. A topical gel comprising
about 0.5% to about 10% Montelukast or pharmaceutically acceptable salt thereof;
about 0.2% to about 8% cellulose polymer; and
about 80% to about 95% amphiphilic compound;
wherein the gel comprises less than 4% water.

Embodiment 43. The topical gel of embodiment 42, wherein the gel comprises about 4% to about 8% Montelukast.

Embodiment 44. The topical gel of any one of embodiments 42 to 43, wherein the gel comprises less than 1% $C_1$-$C_5$ alcohol.

Embodiment 45. The topical gel of any one of embodiments 42 to 42, wherein the gel does not contain $C_1$-$C_5$ alcohol.

Embodiment 46. The topical gel of any one of embodiments 42 to 45, wherein the gel comprises less than 2% water.

Embodiment 47. The topical gel of any one of embodiments 42 to 46, wherein the gel comprises less than 1% water.

Embodiment 48. The topical gel of any one of embodiments 42 to 47, wherein the gel is anhydrous.

Embodiment 49. The topical gel of any one of embodiments 42 to 48, wherein the gel does not comprise a preservative.

Embodiment 50. The topical gel of any one of embodiments 42 to 49, wherein the cellulose polymer comprises hydroxyethylcellulose and hydroxypropyl methylcellulose.

Embodiment 51. The topical gel of any one of embodiments 42 to 50, wherein the cellulose polymer is hydroxypropyl methylcellulose or hydroxypropylcellulose.

Embodiment 52. The topical gel of any one of embodiments 42 to 51, wherein the gel comprises about 2% to about 6% cellulose polymer.

Embodiment 53. The topical gel of any one of embodiments 42 to 52, wherein the gel comprises about 3% to about 4% cellulose polymer.

Embodiment 54. The topical gel of any one of embodiments 42 to 53, wherein the amphiphilic compound comprises oleyl alcohol, polyoxyglycerides, propylene carbonate, propylene glycol, or combinations thereof.

Embodiment 55. The topical gel of embodiment 54, wherein the amphiphilic compound is propylene glycol.

Embodiment 56. The topical gel of embodiment 55, wherein the gel comprises about 85% to about 95% amphiphilic compound.

Embodiment 57. The topical gel of any one of embodiments 42 to 56, wherein total impurities in the gel are less than 2% after 12 months at 25° C.

Embodiment 58. The topical gel of any one of embodiments 42 to 57, wherein the sulfoxide impurity in the gel is less than 2% after 12 months at 25° C.

Embodiment 59. The topical gel of any one of embodiments 42 to 58, wherein the cis-isomer impurity in the gel is less than 0.2% after 12 months at 25° C.

Embodiment 60. The topical gel of any one of embodiments 42 to 59, wherein the methylstyrene impurity in the gel is less than 0.2% after 12 months at 25° C.

Embodiment 61. A method of treating atopic dermatitis comprising administering the topical gel of embodiments 42 to 60.

Embodiment 62. A method of treating erythema comprising administering the topical gel of embodiments 42 to 60.

Embodiment 63. A method of treating pruritus comprising administering the topical gel of embodiments 42 to 60.

Embodiment 64. A method of treating atopic dermatitis comprising topically administering a stable formulation comprising about 0.5% to about 10% Montelukast or pharmaceutically acceptable salt thereof, wherein the formulation is stable for at least 2 weeks.

Embodiment 65. A method of treating erythema comprising topically administering a stable formulation comprising about 0.5% to about 10% Montelukast or pharmaceutically acceptable salt thereof, wherein the formulation is stable for at least 2 weeks Embodiment 66. A method of treating pruritus comprising topically administering a stable formulation comprising about 0.5% to about 10% Montelukast or pharmaceutically acceptable salt thereof, wherein the formulation is stable for at least 2 weeks.

Embodiment 67. The method of any one of embodiments 64 to 66, wherein the stable formulation is a stable emulsion.

Embodiment 68. The method of any one of embodiments 64 to 66, wherein the stable formulation is a topical gel.

Embodiment 69. A method of treating induration in a subject in need thereof, the method comprising topically administering a topical formulation comprising about 0.5% to about 10% Montelukast or pharmaceutically acceptable salt thereof.

Embodiment 70. A method of treating lichenification in a subject in need thereof, the method comprising topically administering a topical formulation comprising about 0.5% to about 10% Montelukast or pharmaceutically acceptable salt thereof.

Embodiment 71. The method of embodiment 67 or embodiment 68, wherein the formulation is stable for at least 2 weeks.

Embodiment 72. A method of reducing the mean IGA score in a population of subjects suffering from atopic dermatitis, the method comprising topically administering to a subject in the population of subjects a Montelukast formulation comprising at least 1% (wt/wt) Montelukast or pharmaceutically acceptable salt thereof for at least 10 days, wherein the mean IGA score is reduced by at least 5% from placebo.

Embodiment 73. A method of reducing the mean % BSA affected score in a subject suffering from atopic dermatitis, the method comprising topically administering to the subject a Montelukast formulation comprising at least 1% (wt/wt) Montelukast or pharmaceutically acceptable salt thereof for at least 10 days, wherein the mean % BSA affected score is reduced by at least 5% from placebo.

Embodiment 74. A method of reducing mean erythema score in a subject suffering from atopic dermatitis, the method comprising topically administering to the subject a Montelukast formulation comprising at least 1% (wt/wt) Montelukast or pharmaceutically acceptable salt thereof for at least 10 days, wherein the mean erythema score is reduced by at least 5% from placebo.

Embodiment 75. A method of reducing mean induration score in a subject suffering from atopic dermatitis, the method comprising topically administering to the subject a Montelukast formulation comprising at least 1% (wt/wt) Montelukast or pharmaceutically acceptable salt thereof for at least 10 days, wherein the mean induration score is reduced by at least 5% from placebo.

Embodiment 76. A method of reducing mean lichenification score in a subject suffering from atopic dermatitis, the method comprising topically administering to the subject a Montelukast formulation comprising at least 1% (wt/wt) Montelukast or pharmaceutically acceptable salt thereof for at least 10 days, wherein the mean lichenification score is reduced by at least 5% from placebo.

Embodiment 77. A method of reducing mean pruritus score in a subject suffering from atopic dermatitis, the method comprising topically administering to the subject a Montelukast formulation comprising at least 1% (wt/wt) Montelukast or pharmaceutically acceptable salt thereof for at least 10 days, wherein the mean pruritus score is reduced by at least 5% from placebo.

Embodiment 78. The method of any one of embodiments 72 to 77, wherein the Montelukast formulation is the topical emulsion of any one of embodiments 1 to 38, or the topical gel of any one of embodiments 42 to 60.

Embodiment 79. A stable topical formulation comprising about 0.5% to about 10% Montelukast or pharmaceutically acceptable salt thereof; wherein the total impurities resulting from the degradation of Montelukast in the composition are less than 2% after 6, 12, 24 or 36 months.

Embodiment 80. The stable topical formulation of embodiment 79, wherein the sulfoxide impurity in the formulation is less than 2% after 12, 24 or 36 months at 25° C. and 60% humidity.

Embodiment 81. The stable topical formulation of embodiments 79 or 80, wherein the cis-isomer impurity in the formulation is less than 1% after 12, 24 or 36 months at 25° C. and 60% humidity.

Embodiment 82. The stable topical formulation of any one of embodiments 79 to 81, wherein the methylstyrene impurity in the formulation is less than 0.2% after 12, 24 or 36 months at 25° C. and 60% humidity.

Embodiment 83. The stable topical formulation of any one of embodiments 79 to 82, wherein the total impurities resulting from the degradation of Montelukast in the composition are less than 2% after 6 months at 40° C. and 75% humidity.

Embodiment 84. The stable topical formulation of any one of embodiments 79 to 83, wherein the sulfoxide impurity in the formulation is less than 2% after 6 months at 40° C. and 75% humidity.

Embodiment 85. The stable topical formulation of any one of embodiments 79 to 84, wherein the cis-isomer impurity in the formulation is less than 1% after 6 months at 40° C. and 75% humidity.

Embodiment 86. The stable topical formulation of any one of embodiments 79 to 85, wherein the methylstyrene impurity in the formulation is less than 0.2% after 6 months at 40° C. and 75% humidity.

Embodiment 87. The stable topical formulation of any one of embodiments 85 or 86, wherein the particle size of particles comprising Montelukast in the emulsion does not change greater than 20% over a period of three months at 25° C., Embodiment 88. A stable topical formulation comprising about 0.5% to about 10% Montelukast or pharmaceutically acceptable salt thereof; wherein the total impurities resulting from the degradation of Montelukast in the composition are less than 2% after 6 months at 40° C. and 75% humidity.

Embodiment 89. The stable topical formulation of embodiment 88, wherein the sulfoxide impurity in the formulation is less than 2% after 6 months at 40° C. and 75% humidity.

Embodiment 90. The stable topical formulation of embodiments 88 or 89, wherein the cis-isomer impurity in the formulation is less than 1% after 6 months at 40° C. and 75% humidity.

Embodiment 91. The stable topical formulation of any one of embodiments 88 to 90, wherein the methylstyrene impurity in the formulation is less than 0.2% after 6 months at 40° C. and 75% humidity.

Embodiment 92. A method of treating atopic dermatitis (AD) in a population of subjects, the method comprising administering a topical pharmaceutical composition comprising 6.5% of Montelukast to a subject in the population of subjects, wherein the administration of the composition results in an improvement in one or more of the following parameters:
- a decrease from baseline in mean Investigator's Global Assessment (IGA) score of at least 20%;
- a decrease from baseline in mean % Body Surface Area (BSA) affected score of at least 20%;
- a decrease from baseline in mean Erythema score of at least 20%;
- a decrease from baseline in mean Induration score of at least 15%;
- a decrease from baseline in mean Lichenification score of at least 25%; and
- a decrease from baseline in mean Pruritus score of at least 20%.

Embodiment 93. A method of treating atopic dermatitis (AD) in a population of subjects, the method comprising administering a topical pharmaceutical composition comprising 6.5% of Montelukast to the subjects, wherein the administration of the composition to the subjects results in an improvement in one or more of the following parameters:
- ≥10% difference between active and placebo in % reduction from baseline for mean Investigator's Global Assessment score;
- ≥10% difference between active and placebo in % reduction from baseline for mean Body Surface Area affected score;
- ≥10% difference between active and placebo in % reduction from baseline for mean Erythema score;
- ≥10% difference between active and placebo in % reduction from baseline for mean Induration score;
- ≥10% difference between active and placebo in % reduction from baseline for mean Lichenification score; and
- ≥10% difference between active and placebo in % reduction from baseline for mean Pruritus score.

Embodiment 94. A method of treating atopic dermatitis (AD) in a group of subjects, the method comprising administering a topical pharmaceutical composition comprising 6.5% of Montelukast to the subjects, wherein the administration of the composition to the subjects results in an improvement in one or more of the following parameters:
- the percentage reduction from baseline in mean IGA score in the population of subjects is at least 5% higher than the percentage reduction in mean IGA score in a separate population of subjects treated with placebo;
- the percentage reduction from baseline in mean % BSA affected score in the population of subjects is at least 5% higher than the percentage reduction in mean % BSA affected score in a separate population of subjects treated with placebo;
- the percentage reduction from baseline in mean Erythema score in the population of subjects is at least 5% higher than the percentage reduction in mean Erythema score in a separate population of subjects treated with placebo;

the percentage reduction from baseline in mean Induration score in the population of subjects is at least 5% higher than the percentage reduction in mean Induration score in a separate population of subjects treated with placebo;

the percentage reduction from baseline in mean Lichenification score in the population of subjects is at least 5% higher than the percentage reduction in mean Lichenification score in a separate population of subjects treated with placebo; and the percentage reduction from baseline in mean Pruritus score in the population of subjects is at least 5% higher than the percentage reduction in mean Pruritus score in a separate population of subjects treated with placebo.

Embodiment 95. A method of treating atopic dermatitis (AD) in a population of subjects, the method comprising administering a topical pharmaceutical composition comprising 6.5% of Montelukast to a subject in the population of subjects, wherein the administration of the composition results in an improvement in one or more of the following parameters:
- at least a 75% reduction from baseline mean IGA score;
- at least an 85% reduction from baseline mean % BSA Affected score;
- at least a 90% reduction from baseline mean Erythema score;
- at least a 90% reduction from baseline mean Induration score;
- at least a 90% reduction from baseline mean Lichenification score; and
- at least an 85% reduction from baseline mean Pruritus score.

Embodiment 96. A method of treating atopic dermatitis (AD) in a population of subjects, the method comprising administering to the population of subjects twice daily a topical pharmaceutical composition comprising 6.5% of Montelukast, wherein the administration of the composition to the population of subjects results in an improvement in one or more of the following parameters:
- the percentage of subjects with a 2- or more grade improvement from baseline is at least 5% higher than placebo in an Investigator's Global Assessment (IGA) score;
- the percentage of subjects with a 2- or more grade improvement from baseline is at least 5% higher than placebo in Erythema score;
- the percentage of subjects with a 1- or more grade improvement from baseline is at least 5% higher than placebo in Induration score;
- the percentage of subjects with a 2- or more grade improvement from baseline is at least 5% higher than placebo in Lichenification score; and
- the percentage of subjects with a 3- or more grade improvement from baseline is at least 5% higher than placebo in Pruritus score.

Embodiment 97. A method of treating atopic dermatitis (AD) in a subject, the method comprising administering a topical pharmaceutical composition comprising 6.5% of Montelukast to the subject, wherein the administration results in a reduction of at least one symptom selected from erythema, pruritus, induration and lichenification compared to a placebo as measured by at least a 2-grade improvement from baseline of the symptoms.

Embodiment 98. A method of treating mild-to-moderate atopic dermatitis (AD) in a patient, the method comprising administering a topical pharmaceutical composition comprising 6.5% of montelukast or its pharmaceutically acceptable salt, twice daily to the patient, wherein the administration of the composition to the patient achieves an Investigator's Global Assessment (IGA) or Investigator's static Global Assessment (ISGA) of "clear" (score=0) or "almost clear" (score=1) with at least two-grade reduction from baseline within week 4 of treatment.

Embodiment 99. The method of any one of the preceding embodiments, wherein the subject is >6 months of age.

Embodiment 100. The method of any one of the preceding embodiments, wherein the subject is ≥12 years of age.

Embodiment 101. The method of any one of the preceding embodiments, wherein the subject is ≥18 years of age.

Embodiment 102. The method of any one of the preceding embodiments, wherein the subject is ≥3 months of age.

Embodiment 103. The method of any one of the preceding embodiments, wherein the subject is without age limitation.

EXAMPLES

Example 1. Topical Emulsions without Carbomer

An oil-in-water topical emulsion was made as outlined in Table 3.

TABLE 3

| Ingredient | % (w/w) |
| --- | --- |
| Montelukast sodium | 5.00 |
| Propylene glycol | 5.00-15.00 |
| DMSO | 7.00-15.00 |
| Preservative | 0.20-1.00 |
| Triglycerides | 8.00-14.00 |
| Glycerol Stearate & PEG-100 Stearate | 1.00-10.00 |
| Purified Water | 50.00-70.00 |
| Cellulose derivative | 0.1-1.0 |
| Strong acid | q.s. |
| | 100% |

Since Montelukast is a highly basic compound, titration with a strong acid was needed to lower the pH of the emulsion to a physiological range. The emulsion made according to Table 3 was physically stable, but Montelukast was not chemically stable in the formulation (data not shown).

Example 2. Topical Emulsion with Carbomer

An oil-in-water emulsion formulation was made as outlined in Table 4.

TABLE 4

| Ingredient | % (w/w) |
| --- | --- |
| Montelukast sodium | 3.00 |
| Alcohol | 5.00-10.00 |
| DMSO | 10.00 |
| Preservative | 0.20-1.00 |
| Polypropylene esters | 4.00-14.00 |
| Fatty acid alcohol | 2.00-8.00 |
| Chelator | 0.05-0.4 |
| Carbomer | 1.00 |
| Purified Water | 50.00-70.00 |
| Emulsifier | 1.00-8.00 |
| | 100% |

Montelukast emulsion was prepared with a carbomer. The emulsion was physically stable.

Example 3. Topical Emulsion without Ethanol

An oil-in-water emulsion formulation was made as outlined in Table 5.

TABLE 5

| Ingredient | % (w/w) |
| --- | --- |
| Montelukast sodium | 3.00 |
| DMSO | 10.00 |
| Preservative | 0.20-1.00 |
| Polypropylene esters | 4.00-14.00 |
| Fatty acid alcohol | 2.00-8.00 |
| Glyceryl Stearate & PEG-100 Stearate | 2.00 |
| Carbomer | 1.00 |
| Purified Water | 50.00-70.00 |
| Emulsifier | 1.00-8.00 |
| | 100% |

Montelukast emulsion was prepared using a carbomer, in the absence of ethanol. The emulsion was physically stable and chemically stable (data not shown).

Example 4. Emulsion with High Concentration of Montelukast

An oil-in-water emulsion formulation was made as outlined in Table 6.

TABLE 6

| Ingredient | % (w/w) |
| --- | --- |
| Montelukast sodium | 6.50 |
| DMSO | 2.50 |
| Preservative | 0.20-1.00 |
| Polypropylene esters | 4.00-14.00 |
| Fatty acid alcohol | 2.00-8.00 |
| Glyceryl Stearate & PEG-100 Stearate | 1.00-5.00 |
| Carbomer | 1.20 |
| Propylene Glycol | 4.00-8.00 |
| Glycerin | 5.00-10.00 |
| Weak acid | 0.10-1.00 |

TABLE 6-continued

| Ingredient | % (w/w) |
| --- | --- |
| Purified Water | 50.00-70.00 |
| Surfactant | 1.00-5.00 |
| | 100% |

Montelukast emulsion was prepared with a carbomer. The emulsion also contained 6.5% Montelukast, and remained physically stable with no aggregates or phase separation detected. The emulsion was additionally chemically stable (data not shown).

Example 5. Emulsion with High Concentration of Montelukast

An oil-in-water emulsion formulation was made as outlined in Table 7 comprising different preservatives.

TABLE 7

| Ingredient | % (w/w) |
| --- | --- |
| Montelukast sodium | 6.50 |
| DMSO | 2.50 |
| Preservative | 0.5-2.0 |
| Polypropylene esters | 4.00-14.00 |
| Fatty acid alcohol | 2.00-8.00 |
| Glyceryl Stearate & PEG-100 Stearate | 2.00 |
| Carbomer | 1.20 |
| Propylene Glycol | 6.30 |
| Simple polyol moisturizer | 5.00-10.00 |
| Weak acid | 0.10-1.00 |
| Purified Water | 50.00-70.00 |
| Surfactant | 1.00-5.00 |
| | 100% |

Example 6. Stability of Montelukast Emulsion

The stability of the Montelukast emulsion was determined over a period of 3 months. The results are presented in Table 8. Impurity C is sulfoxide impurity, Impurity B is a methyl styrene impurity, and Impurity G is a cis-isomer impurity. RT indicates room temperature conditions, INT indicates intermediate conditions, and ACC indicates accelerated conditions.

TABLE 8

| Parameter | T0 | 1 month | | | 2 months | | | 3 months | | |
| --- | --- | --- | --- | --- | --- | --- | --- | --- | --- | --- |
| | | RT | INT | ACC | RT | INT | ACC | RT | INT | ACC |
| Homogeneity | OK | OK | OK | OK | OK | OK | OK | OK | OK | OK |
| Microscopic Appearance (API Crystals) | | up to 20 μm | up to 20 μm | up to 20 μm | | | up to 20 μm | | | |
| Assay % | 96.8% | 95.6% | 95.4% | 95.5% | 95.4% | | 97.0% | 96.8% | | 95.4% |
| Impurity C (%) | 0.08 | 0.09 | 0.09 | 0.11 | 0.08 | | 0.2 | | | |
| Impurity G (%) | | | | | 0.08 | | 0.09 | | 0.15 | 0.17 |
| Impurity B (%) | 0.3 | 0.3 | 0.3 | 0.3 | 0.3 | | 0.28 | 0.32 | | 0.30 |
| Total (%) | 0.41 | 0.39 | 0.39 | 0.41 | 0.51 | | 0.49 | 0.60 | | 0.55 |

Table 8 demonstrates the topical emulsion is physically stable as evidenced by the maintained homogeneity and the lack of Montelukast agglomerates or aggregates. Additionally, the topical emulsion is chemically stable as evidenced by the low levels of sulfoxide impurity, methyl styrene impurity, and cis-isomer impurity.

Example 7. Examples of Various Excipients

To demonstrate the importance of carbomers, and not just the lowering of pH, to the stability of the topical emulsions, various additional oil-in-water topical emulsions were made, using a carbomer, a cellulose derivative, xanthan gum, and other means for lowering pH as outlined in Table 9.

The particle size distribution was tested on the emulsions with xanthan gum and carbomer. The results were similar: D10=6-7 μm, D50=10 μm, and D90=10-12 μm.

All the emulsion formulations were centrifuged with Lumisizer for 16 h, 4000 rpm at 25° C. and the "instability index" was measured. Formulations with instability index close to zero are considered physically stable formulations. The experiment was performed in duplicates (Table 10).

As demonstrated in Table 10, the topical emulsion with carbomer provided the most stable composition compared to emulsions containing hydroxypropyl cellulose (Klucel), Xanthan gum with citric acid and citric acid alone. The emulsion containing carbomer did not have phase separation, showed lower Instability index as determined by Lumi-

TABLE 9

| Description | Example with Carbomer | Replace Carbomer with Klucel | Replace Carbomer with Xanthan Gum | Low concentration Carbomer | Combination of Low concentration Carbomer and Xanthan Gum | Without any polymer. 3% Citric acid | Replace Carbomer with Xanthan Gum. 3% Citric acid |
|---|---|---|---|---|---|---|---|
| Montelukast sodium | 6.50 | 6.50 | 6.50 | 6.50 | 6.50 | 6.50 | 6.50 |
| Glycerin | 7.00 | 7.00 | 7.00 | 7.00 | 7.00 | 7.00 | 7.00 |
| DMSO | 2.50 | 2.50 | 2.50 | 2.50 | 2.50 | 2.50 | 2.50 |
| PPG-15 Stearyl Ether | 8.00 | 8.00 | 8.00 | 8.00 | 8.00 | 8.00 | 8.00 |
| BHT | 0.10 | 0.10 | 0.10 | 0.10 | 0.10 | 0.10 | 0.10 |
| Octyl Dodecanol | 4.00 | 4.00 | 4.00 | 4.00 | 4.00 | 4.00 | 4.00 |
| Carbomer | 1.20 | | | 0.30 | 0.20 | | |
| Klucel MF | | 1.00 | | | | | |
| Xanthan Gum | | | 0.30 | | 0.20 | | 0.30 |
| Propylene Glycol | 6.30 | 6.30 | 6.30 | 6.30 | 6.30 | 6.30 | 6.30 |
| Potassium Sorbate | 0.25 | 0.25 | 0.25 | 0.25 | 0.25 | 0.25 | 0.25 |
| Benzyl Alcohol | 0.50 | 0.50 | 0.50 | 0.50 | 0.50 | 0.50 | 0.50 |
| Citric acid, anhydrous | 0.25 | 0.52 | 0.35 | 0.30 | 0.30 | 3.00 | 3.00 |
| Glyceryl Stearate & PEG-100 Stearate | 2.00 | 2.00 | 2.00 | 2.00 | 2.00 | 2.00 | 2.00 |
| Polysorbate 60 | 3.00 | 3.00 | 3.00 | 3.00 | 3.00 | 3.00 | 3.00 |
| Purified Water | 58.40 | 58.33 | 59.20 | 59.25 | 59.15 | 56.85 | 56.55 |
| Total | 100.00 | 100.00 | 100.00 | 100.00 | 100.00 | 100.00 | 100.00 |

The stability of each of the emulsions made in Table 9 was determined and is presented in Table 10.

sizer and had pH value compatible with the skin over time (preferably between about 4 to 6).

TABLE 10

| Description | Example with Carbomer | Replace Carbomer with Klucel | Replace Carbomer with Xanthan Gum | Low concentration Carbomer | Combination of Low concentration Carbomer and Xanthan Gum | Without any polymer. 3% Citric acid | Replace Carbomer with Xanthan Gum. 3% Citric acid |
|---|---|---|---|---|---|---|---|
| pH of final formula upon preparation | 5.88 | 8.97 | 8.25 | 8.96 | 8.98 | 3.60 | 3.60 |
| pH of final formula upon storage | 5.85 (after 4 days) | 8.91 (after 4 days) | 9.32 (after 4 days) | 9.06 (after 3 days) | 9.26 (after 3 days) | 3.58 | 3.61 |
| Phase separation of final formula | no | Phase separation after 1 day | no | no | no | Agglomeration immediately. API clusters about 2 cm diam. Very sticky. | Agglomeration immediately. API clusters about 1-2 mm diam. Dispersed in bulk |
| Instability index sample 1 | −0.303; | NA* | −4.68; | −2.58; | −4.91; | NA*; | NA*; |
| Instability Sample 2: | −0.258 | NA* | −5.47 | −2.53 | −5.77 | NA* | NA* |

*NA: Instability index cannot be determined due to the agglomeration of the API in the formulation.

The data provides evidence that topical emulsion formulations comprising carbomer unexpectedly provide physical stability and pH values compatible with the skin over time.

Example 8. Various Emulsion Formulations

Various carbomer formulations can be prepared, and are outlined in Table 11, for example. However, the disclosure is not limited to those formulations in Table 11.

TABLE 11

| Formulation 1 | | Formulation 2 | | Formulation 3 | | Formulation 4 | |
|---|---|---|---|---|---|---|---|
| Component | % | Component | % | Component | % | Component | % |
| Montelukast sodium | 6.5 | Montelukast sodium | 6.5 | Montelukast sodium | 6.5 | Montelukast sodium | 6.5 |
| Carbopol 940 NF | 1.2 | Carbopol 971P | 1.8 | Carbopol 934 NF | 1.0 | Carbopol 941 NF | 2.4 |
| Glycerin | 8.0 | Glycerin | 10.0 | Glycerin | 10.0 | Glycerin | 10.0 |
| DMSO | 4.0 | DMSO | 1.5 | DMSO | 2.50 | DMSO | 3.0 |
| Cyclomethicone | 10.0 | Dimethicone | 7.5 | Cyclomethicone | 8.0 | PPG-15 Stearyl Ether | 10.0 |
| Methyl Paraben | 0.4 | Methyl Paraben | 0.4 | Methyl Paraben | 0.4 | Methyl Paraben | 0.4 |
| Propyl Paraben | 0.1 | Propyl Paraben | 0.1 | Propyl Paraben | 0.1 | Propyl Paraben | 0.1 |
| Propylene Glycol | 4.0 | Propylene Glycol | 6.0 | Oleyl alcohol | 4.3 | Oleyl alcohol | 7.2 |
| Benzyl Alcohol | 0.25 | Propyl alcohol | 1.0 | Propyl alcohol | 0.5 | Methanol | 0.5 |
| Citric acid, anhydrous | 1.0 | Acetic acid | 2.5 | Citric acid, anhydrous | 0.5 | Citric acid, anhydrous | 0.5 |
| Glyceryl Stearate & PEG-100 Stearate | 0.25 | Glyceryl Stearate & PEG-100 Stearate | 0.5 | | | | |
| Polysorbate 80 | 2.0 | Polysorbate 40 | 0.5 | Polysorbate 80 | 0.75 | Polysorbate 60 | 0.5 |
| Purified Water | 62.3 | Purified Water | 61.7 | Purified Water | 65.45 | Purified Water | 58.9 |
| Total | 100 | | 100 | | 100 | | 100 |
| Formulation 5 | | Formulation 6 | | Formulation 7 | | Formulation 8 | |
| Component | % | Component | % | Component | % | Component | % |
| Montelukast sodium | 6.5 | Montelukast sodium | 6.5 | Montelukast sodium | 6.5 | Montelukast sodium | 6.5 |
| Carbopol 980 NF | 1.2 | Carbopol 1342 NF | 1.4 | Carbopol 974 P | 0.6 | Carbopol 974P | 1.2 |
| Glycerin | 9.0 | Glycerin | 6.00 | Glycerin | 10.4 | Glycerin | 7.0 |
| Polyethylene glycol | 4.0 | DMSO | 2.5 | Polyethylene glycol | 4.0 | DMSO | 2.5 |
| Dimethicone | 10.0 | Cyclomethicone | 4.5 | PPG-15 Stearyl Ether | 6.5 | PPG-15 Stearyl Ether | 8. |
| Methyl Paraben | 0.4 | BHA | 0.2 | BHT | 0.2 | BHT | 0.1 |
| Propyl Paraben | 0.1 | — | | — | | Octyl Dodecanol | 4.0 |
| Propylene Glycol | 4.0 | Propylene Glycol | 8.1 | Oleyl alcohol | 6.2 | Propylene Glycol | 6.3 |
| Benzyl Alcohol | 0.25 | Benzyl Alcohol | 0.3 | Propanol | 0.4 | Potassium Sorbate 60 | 0.25 |
| Citric acid, anhydrous | 1.0 | Citric acid, anhydrous | 0.5 | Acetic acid | 0.4 | Benzyl Alcohol | 0.5 |
| Glyceryl Stearate & PEG-100 Stearate | 0.25 | Glyceryl Stearate & PEG-100 Stearate | 2.0 | Glyceryl Stearate & PEG-100 Stearate | 1.0 | Citric acid, anhydrous | 0.25 |
| Polysorbate 60 | 2.0 | Polysorbate 80 | 0.1 | Polysorbate 40 | 0.5 | Glyceryl Stearate & PEG-100 Stearate | 2.0 |
| | | | | | | Polysorbate 60 | 3.0 |
| Octyl Dodecanol | 4.0 | Octyl Dodecanol | 4.00 | | | | |
| Purified Water | 57.3 | Purified Water | 63.9 | Purified Water | 63.3 | Purified Water | 58.4 |
| Total | 100 | | 100 | | 100 | Total | 100 |

TABLE 11-continued

| Formulation 9 | | Formulation 10 | | Formulation 11 | | Formulation 12 | |
|---|---|---|---|---|---|---|---|
| Component | % | Component | % | Component | % | Component | % |
| Montelukast sodium | 6.5 | Montelukast sodium | 6.5 | Montelukast sodium | 6.5 | Montelukast sodium | 6.5 |
| Carbopol 981NF | 2.0 | Carbopol 5984 EP | 2.4 | Carbopol 974 P | 3.5 | Carbopol 974P | 2.4 |
| Glycerin | 9.0 | Glycerin | 7.0 | Glycerin | 6.0 | Glycerin | 7.0 |
| Polyethylene glycol | 4.0 | Diethylene glycol monoethyl ether | 4.0 | Diethylene glycol monoethyl ether | 4.0 | Diethylene glycol monoethyl ether | 2.5 |
| PPG-15 Stearyl Ether | 8.0 | Cyclomethicone | 6.0 | Dimethicone | 5.3 | PPG-15 Stearyl Ether | 10.0 |
| Methyl Paraben | 0.40 | BHA | 0.1 | BHA | 0.1 | BHT | 0.1 |
| Propyl Paraben | 0.10 | BHT | 0.1 | BHT | 0.1 | Octyl Dodecanol | 8.0 |
| Propylene Glycol | 4.00 | Oleyl alcohol | 7.0 | Propylene Glycol | 5.0 | Propylene Glycol | 6.3 |
| Benzyl Alcohol | 0.25 | Benzyl Alcohol | 1.5 | Propanol | 1.0 | Potassium Sorbate 60 | 0.25 |
| Citric acid, anhydrous | 1.0 | Acetic acid | 0.75 | Acetic acid | 0.5 | Benzyl Alcohol | 0.5 |
| Glyceryl Stearate & PEG-100 Stearate | 0.25 | Glyceryl Stearate & PEG-100 Stearate | 4.0 | Glyceryl Stearate & PEG-100 Stearate | 3.0 | Citric acid, anhydrous | 0.25 |
| Polysorbate 60 | 2.0 | | | | | Glyceryl Stearate & PEG-100 Stearate | 2.0 |
| Purified Water | 62.5 | Purified Water | 60.65 | Purified Water | 65.0 | Purified Water | 54.2 |
| Total | 100 | | 100 | | 100 | Total | 100 |

Example 9. Topical Gel Formulation

A topical gel was made as outlined in Table 12.

TABLE 12

| Ingredient | % (w/w) |
|---|---|
| Montelukast sodium | 6.50 |
| Fatty acid alcohol | 5.00-10.00 |
| Propylene Glycol | 70.00-92.00 |
| Cellulose derivative | 1.00-6.00 |
| Emulsifier | 1.00-6.00 |
| | 100% |

The topical gel of Table 12 was not chemically stable, as evidenced by the quick formation of impurities as demonstrated in Table 13.

TABLE 13

| Impurity C (sulfoxide impurity) (%) | | | | |
|---|---|---|---|---|
| $T_0$ | 1 month RT | 1 month ACC | 2 months ACC | 6 months ACC |
| 0.14 | 0.20 | 0.40 | 0.61 | 2.03 |

Additionally, the topical gel was not physically stable. Although the Montelukast was soluble at $T_0$, the Montelukast started precipitating in the gel after 2 months at accelerated conditions (data not shown).

Example 10. Topical Gel Formulation

A topical gel was made as outlined in Table 14, wherein a preservative BHA was added in an attempt to increase chemical stability.

TABLE 14

| Ingredient | % (w/w) |
|---|---|
| Montelukast sodium | 6.50 |
| BHA | 0.5-2.5 |
| Fatty acid alcohol | 5.00-10.00 |
| Propylene Glycol | 70.00-92.00 |
| Cellulose derivative | 1.00-6.00 |
| Emulsifier | 1.00-6.00 |
| | 100% |

Additional of the preservative BHA did not improve stability, as evidenced by the formation of impurities as demonstrated in Table 15.

TABLE 15

| Impurity C (sulfoxide impurity) (%) | | | | |
|---|---|---|---|---|
| $T_0$ | 1 month RT | 1 month ACC | 2 months ACC | 6 months ACC |
| 0.25 | 0.49 | 0.97 | 1.53 | 6.65 |

Additionally, the topical gel was not physically stable. Although the Montelukast was soluble at $T_0$, the Montelukast started precipitating in the gel after 1 month (data not shown).

Example 11. Topical Emulsion with Increased Montelukast

A topical emulsion was made as outlined in Table 16.

TABLE 16

| Ingredient | % (w/w) |
|---|---|
| Montelukast sodium | 8.00 |
| Glycerin | 5.00-10.00 |
| DMSO | 2.50 |
| Preservative | 0.1-0.3 |
| Polypropylene esters | 4.00-14.00 |
| Long-chain fatty alcohol | 2.00-6.00 |
| Carbomer | 1.00 |
| Propylene Glycol | 4.00-8.00 |
| Purified Water | 50.00-70.00 |
| Weak acid | 0.10-1.00 |
| Acrylamide/sodium acryloyldimethyl taurate copolymer | 3.00-5.00 |

The topical emulsion of Table 16 was shown to be physically stable for at least three months under standard conditions (data not shown).

Example 12. Topical Gel Formulation

A topical gel was prepared as outlined in Table 17,

TABLE 17

| Ingredient | % (w/w) |
|---|---|
| Montelukast sodium | 6.5 |
| Propylene Glycol | 83.5%-92.5% |
| Cellulose derivative | 1.00-10.00 |
| | 100% |

The topical gel as formulated in Table 17 was shown to be both chemically and physically stable over an extended period of time as shown in Table 18.

TABLE 18

| Parameter | T0 | 1 month | | | 2 months | | | 3 months | | |
|---|---|---|---|---|---|---|---|---|---|---|
| | | RT | INT | ACC | RT | INT | ACC | RT | INT | ACC |
| Homogeneity | OK | OK | OK | OK | OK | OK | OK | OK | OK | OK |
| Microscopic Appearance (API Crystals) | No | No | No | No | No | No | No | | | |
| Assay % (90-110) | 96.5 | 96.8 | 97.2 | 96.7 | 101.2 | 100.3 | 100.7 | 98.4 | 98.7 | 98.0 |
| Impurity C-sulfoxide (%) | 0.08 | 0.08 | 0.1 | 0.11 | 0.12 | 0.13 | 0.19 | 0.16 | 0.17 | 0.26 |
| Impurity G- cis isomer (%) | 0.05 | 0.06 | 0.06 | 0.05 | | | | | | |
| Impurity B-methyl styrene (%) | 0.08 | 0.08 | 0.08 | 0.08 | 0.08 | 0.09 | 0.09 | 0.1 | 0.13 | 0.11 |
| Total Impurities (%) | 0.26 | 0.41 | 0.47 | 0.66 | 0.35 | 0.37 | 0.47 | 0.35 | 0.53 | 0.67 |

Thus, the topical gel of the present disclosure provides for physical stability as well as chemical stability.

Example 13. Stability Comparison of Topical Emulsion and Topical Gel to Other Emulsions Applicant compared the topical emulsion of the present disclosure to the emulsions reported in WO 2019/007356 (Example 8 and Example 9). The topical emulsions disclosed in WO 2019/007356 (Example 8 and Example 9) do not comprise a carbomer as featured in the present disclosure. The results presented in Table 19 are for T=0.

TABLE 19

| Parameter | WO 2019/007356 example 8 | WO 2019/007356 example 9 | Topical Emulsion (Carbomer Formulation) | Topical Gel |
|---|---|---|---|---|
| Homogeneity | No phase separation. Grainy consistency. After 24 hours non-homogeneous | No phase separation. Grainy consistency. After 24 hours non-homogeneous | Homogeneous | Homogeneous |
| Assay % (90-110%) | 97.9 | 94.4 | 96.8 | 96.5 |

TABLE 19-continued

| Parameter | WO 2019/007356 example 8 | WO 2019/007356 example 9 | Topical Emulsion (Carbomer Formulation) | Topical Gel |
|---|---|---|---|---|
| Impurity C Sulfoxide (%) | 0.50** | 0.75** | 0.08 | 0.08 |
| Total Impurities (%) | 0.80 | 1.47** | 0.41 | 0.26 |

**indicates out of desired specification

Table 19 demonstrates the topical emulsions disclosed in WO 2019/007356 are not physically stable even after 24 hours as evidenced by the non-homogeneous consistency. Additionally, the topical emulsions disclosed in WO 2019/007356 are not chemically stable as evidenced by the appearance of impurities.

Example 14. Stability Comparison of Topical Emulsion to Other Topical Solutions

Applicant compared the topical emulsion of the present disclosure (Carbomer Formulation) to the solutions reported in WO 2010/104281 (Table 1 and Table 2). The solutions in WO 2010/104281 were prepare by dissolving Montelukast in a solution comprising ethanol:propylene glycol at a ratio of 7:3. The Montelukast was present at 0.5%, 1%, 2% (Table 1) or 14%. 26% or 36% (Table 2). The results of WO 2010/104281 and the present disclosure (Carbomer Formulation) are presented in Table 20.

TABLE 20

| | Analytical Parameter, % | T0 | 1 month RT | 1 month ACC |
|---|---|---|---|---|
| WO 2010/ 104281 Topical solution | Assay (90-110%) | 98.1 | 96.4 | 95.4 |
| | Sulfoxide Impurity (%) | NA | 1.99 | 2.87 |
| | Cis-isomer Impurity (%) | 0.08 | 0.93 | 1.19 |
| | Methylstyrene Impurity (%) | 0.3 | 0.3 | 0.3 |
| | Total Impurity (%) | 0.38 | 3.2 | 4.4 |

TABLE 20-continued

| | Analytical Parameter, % | T0 | 1 month RT | 1 month ACC |
|---|---|---|---|---|
| Carbomer Formulation | Assay (90-110%) | 96.3 | 100.7 | 100.9 |
| | Sulfoxide Impurity (%) | 0.07 | 0.12 | 0.14 |
| | Cis-isomer Impurity (%) | 0.12 | <0.05 | <0.05 |
| | Methylstyrene Impurity (%) | 0.10 | 0.08 | 0.08 |
| | Total Impurity (%) | 0.35 | 0.20 | 0.22 |

Table 20 provides additional support that topical emulsions comprising Montelukast and carbomers are more stable than topical formulations previously reported, as evidenced by the low levels of sulfoxide impurity, methyl styrene impurity, and cis-isomer impurity.

Example 15. Long Term Stability Analysis

As demonstrated previously in Example 6, Table 8, the topical emulsion of the present disclosure provides increased stability for up to three months, even under accelerated storage conditions. As demonstrated previously in Example 12, Table 18, the topical gel of the present disclosure provides increased stability for up to three months, even under accelerated storage conditions.

The stability of the topical emulsion of Example 5 and the topical gel of Example 12 was further investigated for up to 12 months. The 6-month and the 9-month stability data are also presented in Table 21.

TABLE 21

| | Analytical Parameter, % | 6 months | | | 9 months | | 12 months | | 24 months |
|---|---|---|---|---|---|---|---|---|---|
| | | ACC | INT | RT | INT | RT | INT | RT | RT |
| Emulsion formulation | Assay (90-110) | 99.9 | 98.0 | 98.1 | 98.5 | 99.1 | 104.4 | 104.9 | 100.6 |
| | Sulfoxide Impurity (%) | 0.26 | 0.19 | 0.16 | 0.20 | 0.17 | 0.28 | 0.22 | 0.26 |
| | Cis-isomer Impurity (%) | <0.05 | <0.05 | <0.05 | <0.05 | <0.05 | <0.05 | <0.05 | <0.1 |
| | Methylstyrene Impurity (%) | 0.07 | 0.07 | 0.07 | 0.10 | 0.09 | 0.07 | 0.07 | <0.1 |
| | Total Impurity (%) | 0.40 | 0.32 | 0.28 | 0.32 | 0.31 | 0.41 | 0.4 | 0.34 |
| Gel formulation | Assay (90-110) | 95.2 | 95.2 | 95.7 | 95.8 | 97.9 | 103.6 | 104.1 | ND |
| | Sulfoxide Impurity (%) | 0.29 | 0.17 | 0.15 | 0.21 | 0.16 | 0.26 | 0.2 | ND |

TABLE 21-continued

| Analytical Parameter, % | 6 months | | | 9 months | | 12 months | | 24 months |
|---|---|---|---|---|---|---|---|---|
| | ACC | INT | RT | INT | RT | INT | RT | RT |
| Cis-isomer Impurity (%) | <0.05 | <0.05 | <0.05 | <0.05 | <0.05 | <0.05 | 0.07 | ND |
| Methylstyrene Impurity (%) | 0.10 | 0.09 | 0.09 | 0.09 | 0.09 | 0.09 | 0.09 | ND |
| Total Impurity (%) | 0.61 | 0.49 | 0.35 | 0.54 | 0.39 | 0.78 | 0.63 | ND |

ND- not determined

Table 21 provides evidence that the topical emulsion and the topical gel as provided herein are chemically stable for up to 12 months in both RT and INT conditions.

Without being bound by any theory, in some embodiments the carbomer contributes to physiochemical stability of the formulation.

Example 16: Emulsion with Reduced Globule Size

The formulations containing Carbomer used in the globule size analysis appear for example in Table 9- and in Table 11. The comparative formulation (Example 14 as disclosed in U.S. Pat. No. 10,548,837) is as found in Table 22:

TABLE 22

Comparative formulation: Montelukast in a cream formulation

| Ingredient | % W/W |
|---|---|
| Montelukast sodium | 5% |
| Propylene glycol | 10% |
| DMSO | 10% |
| Methylparaben | 0.3% |
| Propylparaben | 0.1% |
| BHT | 0.1% |
| MCT | 10% |
| Glyceryl Stearate & PEG-100 Stearate | 5% |
| Purified water | 59.1% |
| Natrosol 250 HEC HHX | 0.30% |
| EDTA | 0.1% |
| HCl (10% sol) | q.s. |

Sample Preparation Procedure:

Prior to performing the globule size analysis of a sample, a clean glass microscope slide and cover slip (that later will be used for the sample) were placed on the microscope and their cleanness was assess under magnifying lens. A sample from an emulsion without carbomer (Comparative formulation above) and a sample from an emulsion comprising carbomer (Table 9) was taken from 2-3 different areas in the container in which they were stored (sample from the depth of the product not from the surface) and transferred onto a microscope slide. A cover slip was placed over the sample and pressed gently in order to spread the sample thoroughly.

A magnification of ×50 was used. The sample was focused in a manner that properly showed the globule particles and crystals.

Globule Assessment Using Nikon Eclipse ciPOL Microscope Under Non Polarized Light Two samples were examined under the microscope using suitable magnification (suitable objective size). Two fields of view were evaluated for each sample. Air, oil and water globules were distinguished from each other. The largest globules in a field of view were measured and the size was recorded in the report. Using this method, it was determined that the sample from an emulsion without carbomer (Comparative formulation) had a maximum globule size of 458 while the sample from an emulsion comprising carbomer (Table 9) had a maximum globule size of 8 μm.

The correlation between the type of polymer and the globule size of various formulation batches prepared by two different processes was determined. The results are presented in Table 23.

TABLE 23

| Batch | Prototype | % polymer | Globule size (um) |
|---|---|---|---|
| 1 | Example 14 as disclosed in U.S. Pat. No. 10,548,837 (o/w emulsion) | HEC 0.3% | Up to 458 |
| 2 | o/w emulsion with Carbomer - first batch | Carbomer 1.2% | Up to 8 |
| 3 | o/w emulsion with Carbomer - second batch | Carbomer 1.2% | Up to 5 |
| 4 | o/w emulsion with lower concentration of Carbomer | Carbomer 0.4% | Up to 16 |

HEC = hydroxyethyl cellulose

Table 23 demonstrates that globule size of formulations depends on type of polymer and its concentration in the formulations.

Conclusions:

Emulsion formulations with carbomer provides a smaller globule size relative to emulsion formulations with cellulose at almost similar concentration. Small globule size of the emulsion of the invention can be advantageous with respect to formulation long-term stability. Droplet size is one of the important characteristics of the topical formulation that contributes to the physical stability of dermal and cosmetic products. The small droplet size prevents the droplet coalescence and sedimentation against gravitational force.

Example 17: Double Blind Clinical Study of 6.5% Montelukast Topical Cream

A multi-center, double-blind, randomized, placebo-controlled study using a Montelukast cream as described herein (6.5%) was conducted. Patients experiencing mild or moderate atopic dermatitis were randomized to receive twice daily applications of active cream or its vehicle for 28 days. The percent change from baseline in Investigator Global Assessment (IGA) score, Body Surface Area (BSA) affected score, erythema score, induration score, lichenification score, and pruritus score was determined following 14- and 28-days of treatment. The results presented in Table 24 demonstrate Montelukast was statistically superior to its vehicle in % reduction from baseline scores for IGA, erythema, pruritus, induration and affected % BSA by Day 14 and IGA, erythema, pruritus, lichenification and affected % BSA by Day 28. The results of the clinical study indicated Topical Montelukast was safe and well-tolerated following 28 days of treatment. Specifically, at least 60% of the patients reported either absent or mild Dryness and Scaling at week 4 of treatment, and at least 60% of the patients reported absent of Erosion at week 4 of treatment.

TABLE 24

| Clinical parameter | Treatment Difference (Active-Placebo) in Mean % Reduction from Baseline Score | |
|---|---|---|
| | Week 2 | Week 4 |
| IGA[1] score | Δ21%*** | Δ23%*** |
| % BSA Affected | Δ24%*** | Δ17%*** |
| Erythema[2] score | Δ34%*** | Δ31%*** |
| Induration[2] score | Δ20%* | Δ13% |
| Lichenification[2] score | Δ15% | Δ29%*** |
| Pruritis[3] score | Δ18%** | Δ17%*** |

[1]5-point IGA scale of Disease Severity for AD; score 0 'clear', 1 'almost clear', 2 'mild', 3 'moderate' and 4 'severe'

[2]4-point severity scale used for erythema, induration, lichenification; score 0 'none', 1 'mild', 2 'moderate', and 3 'severe'

[3]11-point scale used for pruritus self-assessment 0 'no itch' up to 10 'worst imaginable itch'

*$p < 0.05$

**$p < 0.01$

***$p < 0.001$

The actual numerical reduction from baseline for each 6.5% Montelukast topical cream (6.5%) and placebo is as follows:

TABLE 25

| | | Montelukast cream (6.5%) | Placebo | p-value |
|---|---|---|---|---|
| % change from baseline to Day 28 | IGA | −88.2% | −64.6% | p < 0.0001 |
| | % BSA Affected | −90.2% | −73.5% | p < 0.0001 |
| | Erythema | −93.8% | −62.5% | p = 0.0002 |
| | Induration | −95.8% | −83.3% | p = 0.0614 |
| | Lichenification | −93.8% | −64.6% | p = 0.0006 |
| | Pruritus | −89.3% | −72.4% | p = 0.0003 |

Montelukast cream was safe and well-tolerated in the mild to moderate atopic dermatitis adult patients studied. No treatment-emergent adverse events were reported and all subjects completed the study. Actively-assessed application site signs and symptoms including scaling, dryness and erosion were predominantly absent or mild at the end of the 28-day treatment, while burning/stinging and pain were completely absent. Seven and six occurrences of 'moderate' severity application site signs and symptoms were reported from the Montelukast cream and vehicle groups, respectively, following the start of treatment while no 'severe' application site signs and symptoms were reported following the start of treatment.

The success proportion for this study is presented below in Table 26.

TABLE 26

| Endpoint | Montelukast Topical Cream, 6.5% | Placebo |
|---|---|---|
| PRIMARY ENDPOINT IGA Success Proportion | | |
| Day 28 (success ≥2) | 87.50% | 62.50% |
| SECONDARY ENDPOINT IGA Success Proportion | | |
| Day 14 (success ≥1) | 91.67% | 70.83% |
| Day 28 (success ≥1) | 100.00% | 100.00% |
| BSA % Reduction | | |
| Day 14 | 64.95% | 40.56% |
| Day 28 | 90.18% | 73.46% |
| Erythema Success Proportion | | |
| Day 14 (success ≥1) | 87.50% | 62.50% |
| Day 14 (success ≥2) | 33.33% | 0.00% |
| Day 28 (success ≥1) | 100.00% | 87.50% |
| Day 28 (success ≥2) | 75.00% | 12.50% |
| Induration Success Proportion | | |
| Day 14 (success ≥1) | 75.00% | 62.50% |
| Day 14 (success ≥2) | 16.67% | 12.50% |
| Day 28 (success ≥1) | 100.00% | 95.83% |
| Day 28 (success ≥2) | 41.67% | 41.67% |
| Lichenification Success Proportion | | |
| Day 14 (success ≥1) | 70.83% | 62.50% |
| Day 14 (success ≥2) | 12.50% | 4.17% |
| Day 28 (success ≥1) | 100.00% | 83.33% |
| Day 28 (success ≥2) | 45.83% | 20.83% |
| Pruritus Success Proportion | | |
| Day 14 (success ≥3) | 70.83 | 58.33 |
| Day 28 (success ≥3) | 100.00 | 100.00 |

Success proportions defined by stated point improvement on respective ratings scales (e.g., ≥1-, ≥2-, ≥3-, ≥4-grade improvement).

Montelukast Levels in Blood:

Low systemic exposure was detected following twice daily topical application of Montelukast 6.5% cream, with Day 14 plasma values below detectable levels in the vast majority of mild to moderate AD patients studied. Only 2 subjects had quantifiable montelukast levels of 2.93 ng/mL and 2.60 ng/mL. No systemic adverse events were noted, including no clinically significant changes in vitals sign measurements and no adverse events of interest for the class of drugs (including no neuropsychiatric events) were reported.

Example 18: Double Blind Placebo Controlled Parallel-Group Clinical Study of 6.5% Montelukast Topical Cream A multi-center, double-blind, randomized, placebo-controlled, parallel-group study using a Montelukast cream as described herein (6.5%) is conducted. Patients experiencing mild or moderate atopic dermatitis are administered either (i) the cream or (ii) placebo (1:1 ratio) two times a day for 28 days to the affected area. A comparison of the Montelukast to placebo is determined by six different endpoints including Investigator Global Assessment (IGA), Body Surface Area (BSA), erythema, induration, lichenification, and pruritus on days 0, 14 and 28.

The primary endpoint includes the number of subjects with a clinical response (IGA) of "success" at week 4.

Success is defined as an IGA score that is at least 2 grades less than the baseline assessment.

Secondary endpoints include:
(i) The number of subjects with IGA at least 1 grade less than the baseline assessment at week 2 and at week 4;
(ii) Change from baseline in % BSA affected at week 2 and a week 4;
(iii) The number of subjects with at least 1 grade less than the baseline assessment for each of the individual Signs and Symptoms of AD (i.e., erythema, induration/papulation, lichenification) at week 2 and at week 4;
(iv) The number of subjects with at least 2 grades less than the baseline assessment for each of the individual Signs and Symptoms of AD (i.e., erythema, induration/papulation, lichenification) at week 2 and at week 4;
(v) The number of subjects with Numerical Rating Scale of pruritus at least 3 points less than the baseline assessment at week 2 and at week 4;

It is expected that administration of the montelukast cream will result in success of the primary endpoint as well as the secondary endpoint.

Example 19: Double Blind Clinical Study of 6.5% Montelukast Topical Cream for 8 Weeks A multi-center, double-blind, randomized, placebo-controlled study using a Montelukast cream as described herein (6.5%) is conducted. Selected subjects are 12 years and older experiencing mild or moderate atopic dermatitis, as defined as a score of 2 or 3 on the Investigator's Static Global Assessment (ISGA), with an affected Body Surface Area (BSA) involvement of 3%-20%.

ISGA is assessed as follows in Table 27:

TABLE 27

Investigator's Static Global Assessment (ISGA)

| Score | Grade | Description |
| --- | --- | --- |
| 0 | Clear | Minor residual hypo/hyperpigmentation; no erythema or induration/papulation; no oozing/crusting. |
| 1 | Almost Clear | Trace faint pink erythema, with barely perceptible induration/papulation and no oozing/crusting |
| 2 | Mild | Faint pink erythema and mild induration/papulation and no oozing/crusting |
| 3 | Moderate | Pink-red erythema with moderate induration/papulation with or without oozing/crusting |
| 4 | Severe | Deep or bright red erythema with severe induration/papulation and with oozing/crusting |

The EASI is a scale used in clinical trials to assess the severity and extent of atopic dermatitis (AD). In EASI, four disease characteristics of AD (erythema, infiltration/papulation, excoriations, and lichenification) are assessed for severity by the investigator on a scale of 0 (absent) to 3 (severe). It has been suggested that the severity of AD based on EASI score should be categorized as follows: 0=clear; 0.1 to 1.0=almost clear; 1.1 to 7.0=mild; 7.1 to 21.0=moderate; 21.1 to 50.0=severe; 50.1 to 72.0=very severe. EASI-75 indicates ≥75% improvement from baseline.

It is expected that there will be at least ≥5% difference between active and placebo treatments in EASI-75.

Subjects are administered to one arm the cream twice daily for 56 days. The opposing arm is administered a vehicle placebo. Efficacy will be evaluated using a 5-point Investigator's Static Global Assessment (ISGA) for disease severity, % BSA affected, Eczema Area and Severity Index (EAST), Pruritus-NRS. Patient-Reported Outcomes captured will include Patient Global Impression of Treatment, Patient Global Impression of Change and Dermatology Life Quality Index (DLQI). Safety will be evaluated by treatment emergent adverse events and active assessment of Local Skin Reactions (erythema, dryness, etc.).

It is expected that topical treatment with Montelukast cream will result in an improvement of one or more of the listed parameters, and potentially each of the parameters compared to placebo.

All references cited herein, including patents, patent applications, papers, textbooks and the like, and the references cited therein, to the extent that they are not already, are hereby incorporated herein by reference in their entirety.

What is claimed is:

1. A method of treating atopic dermatitis (AD) in a population of subjects, the method comprising administering a topical pharmaceutical composition comprising 6.5% of Montelukast to a subject in the population of subjects, wherein the administration of the composition results in an improvement in one or more of the following parameters:
   a. a decrease from baseline in mean Investigator's Global Assessment (IGA) score of at least 20%;
   b. a decrease from baseline in mean % Body Surface Area (BSA) affected score of at least 20%;
   c. a decrease from baseline in mean Erythema score of at least 20%;
   d. a decrease from baseline in mean Induration score of at least 15%;
   e. a decrease from baseline in mean Lichenification score of at least 25%; and
   f. a decrease from baseline in mean Pruritus score of at least 20%.

2. A method of treating atopic dermatitis (AD) in a population of subjects, the method comprising administering a topical pharmaceutical composition comprising 6.5% of Montelukast to a subject in the population of subjects, wherein the administration of the composition results in an improvement in one or more of the following parameters:
   a. ≥10% difference between active and placebo in % reduction from baseline for mean Investigator's Global Assessment score;
   b. ≥10% difference between active and placebo in % reduction from baseline for mean % Body Surface Area affected score;
   c. ≥10% difference between active and placebo in % reduction from baseline for mean Erythema score;
   d. ≥10% difference between active and placebo in % reduction from baseline for mean Induration score;
   e. ≥10% difference between active and placebo in % reduction from baseline for mean Lichenification score; and
   f. ≥10% difference between active and placebo in % reduction from baseline for mean Pruritus score.

3. A method of treating atopic dermatitis (AD) in a population of subjects, the method comprising administering a topical pharmaceutical composition comprising 6.5% of Montelukast to a subject in the population of subjects, wherein the administration of the composition to the subject results in an improvement in one or more of the following parameters:
   a. the percentage reduction from baseline in mean IGA score in the population of subjects is at least 5% higher than the percentage reduction in mean IGA score in a separate population of subjects treated with placebo;
   b. the percentage reduction from baseline in mean % BSA affected score in the population of subjects is at least 5% higher than the percentage reduction in mean % BSA affected score in a separate population of subjects treated with placebo;
c. the percentage reduction from baseline in mean Erythema score in the population of subjects is at least 5% higher than the percentage reduction in mean Erythema score in a separate population of subjects treated with placebo;
d. the percentage reduction from baseline in mean Induration score in the population of subjects is at least 5% higher than the percentage reduction in mean Induration score in a separate population of subjects treated with placebo;
e. the percentage reduction from baseline in mean Lichenification score in the population of subjects is at least 5% higher than the percentage reduction in mean Lichenification score in a separate population of subjects treated with placebo; and
f. the percentage reduction from baseline in mean Pruritus score in the population of subjects is at least 5% higher than the percentage reduction in mean Pruritus score in a separate population of subjects treated with placebo.

4. A method of treating atopic dermatitis (AD) in a population of subjects, the method comprising administering a topical pharmaceutical composition comprising 6.5% of Montelukast to a subject in the population of subjects, wherein the administration of the composition results in an improvement in one or more of the following parameters:
a. at least a 75% reduction from baseline mean IGA score;
b. at least an 85% reduction from baseline mean % BSA Affected score;
c. at least a 90% reduction from baseline mean Erythema score;
d. at least a 90% reduction from baseline mean Induration score;
e. at least a 90% reduction from baseline mean Lichenification score; and
f. at least an 85% reduction from baseline mean Pruritus score.

5. A method of treating atopic dermatitis (AD) in a population of subjects, the method comprising administering to the population of subjects twice daily a topical pharmaceutical composition comprising 6.5% of Montelukast, wherein the administration of the composition to the population of subjects results in an improvement in one or more of the following parameters:

a. the percentage of subjects with a 2-or more grade improvement from baseline is at least 5% higher than placebo in Investigator's Global Assessment (IGA) score;
b. the percentage of subjects with a 2-or more grade improvement from baseline is at least 5% higher than placebo in Erythema score;
c. the percentage of subjects with a 1-or more grade improvement from baseline is at least 5% higher than placebo in Induration score;
d. the percentage of subjects with a 2-or more grade improvement from baseline is at least 5% higher than placebo in Lichenification score; and
e. the percentage of subjects with a 3-or more grade improvement from baseline is at least 5% higher than placebo in Pruritus score.

6. A method of treating atopic dermatitis (AD) in a subject, the method comprising administering a topical pharmaceutical composition comprising 6.5% of Montelukast to the subject, wherein the administration results in a reduction of at least one symptom selected from erythema, pruritus, induration and lichenification compared to a placebo as measured by a success profile comprising at least a 2-grade improvement from baseline of the symptoms.

7. A method of treating mild-to-moderate atopic dermatitis (AD) in a patient, the method comprising administering a topical pharmaceutical composition comprising 6.5% of montelukast or its pharmaceutically acceptable salt, twice daily to the patient, wherein the administration of the composition to the patient achieves an Investigator's Global Assessment (IGA) or Investigator's static Global Assessment (ISGA) of "clear" (score=0) or "almost clear" (score=1) with at least two-grade reduction from baseline within week 4 of treatment.

8. The method of claim 7, wherein the subject is ≥6 months of age.

9. The method of claim 7, wherein the subject is ≥12 years of age.

10. The method of claim 7, wherein the subject is ≥18 years of age.

11. The method of claim 7, wherein the subject is ≥3 months of age.

* * * * *